(12) United States Patent
DuMontelle et al.

(10) Patent No.: US 8,821,570 B2
(45) Date of Patent: Sep. 2, 2014

(54) ADJUSTABLE ANNULOPLASTY RING WITH SUBCUTANEOUS ACTIVATION PORT

(75) Inventors: Jeffrey P. DuMontelle, Irvine, CA (US); Maurice Buchbinder, La Jolla, CA (US); Samuel M. Shaolian, Newport Beach, CA (US); Ninh H. Dang, Trabuco Canyon, CA (US); Paul A. Molloy, San Clemente, CA (US); Ross Tsukashima, San Diego, CA (US); Brian C. Gray, Lake Forest, CA (US); Daniel C. Anderson, Pomona, CA (US)

(73) Assignee: MiCardia Corporation, Irvine, CA (US)

( * ) Notice: Subject to any disclaimer, the term of this patent is extended or adjusted under 35 U.S.C. 154(b) by 330 days.

(21) Appl. No.: 13/386,331

(22) PCT Filed: Jul. 20, 2010

(86) PCT No.: PCT/US2010/042644
§ 371 (c)(1),
(2), (4) Date: Mar. 16, 2012

(87) PCT Pub. No.: WO2011/011443
PCT Pub. Date: Jan. 27, 2011

(65) Prior Publication Data
US 2012/0197392 A1    Aug. 2, 2012

Related U.S. Application Data

(60) Provisional application No. 61/227,014, filed on Jul. 20, 2009.

(51) Int. Cl.
*A61F 2/24* (2006.01)
*A61L 27/50* (2006.01)

(52) U.S. Cl.
CPC ............. *A61L 27/50* (2013.01); *A61F 2/2445* (2013.01); *A61L 27/507* (2013.01); *A61F 2250/001* (2013.01); *A61F 2210/0023* (2013.01); *A61F 2210/0033* (2013.01)
USPC ........................................................ 623/2.37

(58) Field of Classification Search
USPC ........................................................ 623/2.37
See application file for complete search history.

(56) References Cited

U.S. PATENT DOCUMENTS

| | | | | |
|---|---|---|---|---|
| 4,995,389 A | * | 2/1991 | Harris | 607/37 |
| 5,205,286 A | * | 4/1993 | Soukup et al. | 600/377 |
| 5,695,518 A | | 12/1997 | Laerum | |
| 6,053,891 A | * | 4/2000 | DeCampli | 604/288.01 |

(Continued)

OTHER PUBLICATIONS

Notification of Transmittal of the International Search Report and Written Opinion of the International Searching Authority or the Declaration, for PCT/US2010/042644, filed Jul. 20, 2010.

*Primary Examiner* — Thomas J Sweet
*Assistant Examiner* — Megan Wolf
(74) *Attorney, Agent, or Firm* — Stoel Rives LLP

(57) ABSTRACT

Annuloplasty rings are employed to treat heart valve defects, such as regurgitation. Synching the heart tissue to the ring restores the valve opening to its approximate original size and operating efficiency. Adjustable annuloplasty rings allow for a proper degree of synching both during open heart surgery and over the patient's lifetime. A subcutaneous port may be coupled to an adjustable annuloplasty ring such that an external activation energy generator can be used to heat the adjustable annuloplasty ring and thereby adjust the size of the annuloplasty ring.

42 Claims, 18 Drawing Sheets

(56) References Cited

U.S. PATENT DOCUMENTS

| | | |
|---|---|---|
| 7,722,668 B2 | 5/2010 | Moaddeb et al. |
| 2004/0133269 A1 | 7/2004 | Bruckheimer et al. |
| 2005/0070991 A1 | 3/2005 | Pienknagura |
| 2005/0283095 A1 | 12/2005 | Nair et al. |
| 2006/0247584 A1* | 11/2006 | Sheetz et al. ............. 604/288.02 |
| 2007/0135913 A1* | 6/2007 | Moaddeb et al. ............ 623/2.37 |
| 2007/0276478 A1* | 11/2007 | Marmureanu et al. ....... 623/2.11 |

* cited by examiner

ADJUSTABLE ANNULOPLASTY RING WITH SUBCUTANEOUS ACTIVATION PORT

RELATED APPLICATIONS

This application claims priority under 35 U.S.C. §371 to International Application No. PCT/US2010/042644, filed Jul. 20, 2010, which claims the benefit of U.S. Provisional Patent Application No. 61/227,014, filed Jul. 20, 2009, each of which is hereby incorporated by reference herein in its entirety.

TECHNICAL FIELD

The present disclosure relates to annuloplasty rings. In particular, the present disclosure relates to adjustable annuloplasty rings that may be coupled to subcutaneous ports for coupling the annuloplasty rings to external energy sources, such as a radio frequency generators.

BACKGROUND INFORMATION

Heart valve defects, such as regurgitation, may be caused by a relaxation of the tissue surrounding the valve. This causes the valve opening to enlarge, which prevents the valve from sealing properly. Such heart conditions are commonly treated by sewing an annuloplasty ring around the valve. Synching the tissue to the ring restores the valve opening to its approximate original size and operating efficiency.

The proper degree of synching, however, is difficult to determine during open heart surgery. This is due to the fact that the patient is under general anesthesia, in a prone position, with the chest wide open, and with a large incision in the heart. These factors affect the normal operation of the valve. Even if the synching is done well, the tissue may continue to relax over the patient's lifetime such that the heart condition returns.

An adjustable annuloplasty ring allows for the proper degree of synching both during open heart surgery and over the patient's lifetime. A subcutaneous adjustment system may be located such that a simple incision will allow access to the adjustment system. The ring prosthesis modification can be done at early onset of recurring regurgitation, with no discomfort to the patient, to stop disease progression with just a simple procedure without a hospital stay, and without a need for an invasive procedure or prolonged anesthesia. The systems and methods disclosed herein are applicable to mitral regurgitation and tricuspid regurgitation using similar construction, design, and numbers of components except for specific routing differences between the mitral valve and the tricuspid valve. The system and methods disclosed herein may also be used for other heart valves.

Certain adjustable annuloplasty rings are described, for example, in U.S. Pat. No. 7,722,668, issued to Moaddeb et al. on May 25, 2010, which is assigned to the assignee of the present disclosure, and which is incorporated by reference herein. Such adjustable annuloplasty rings may include a body member comprising a shape memory material that is responsive to changes in temperature and/or exposure to a magnetic field. Various techniques have been tried for transmitting an activation energy to an annuloplasty ring implanted within a patient's heart to provide the change in temperature and/or exposure to the magnetic field for changing the shape of the body member.

SUMMARY OF THE DISCLOSURE

In one embodiment, annuloplasty ring assembly includes an adjustable annuloplasty ring having a body member comprising shape memory material to change a dimension of the adjustable annuloplasty ring in response to application of an activation energy. The annuloplasty ring assembly also includes a subcutaneous activation cable to provide the activation energy to the shape memory material of the adjustable annuloplasty ring. The subcutaneous activation cable includes a first end coupled to the adjustable annuloplasty ring, and a second end comprising a subcutaneous connector including a first plurality of electrodes. The annuloplasty ring assembly further includes a subcutaneous port implantable in subcutaneous tissue within a patient. The subcutaneous port includes a first interface to receive the subcutaneous connector of the subcutaneous activation cable, a second interface to receive a transcutaneous connector inserted through the patient's skin, the transcutaneous connector providing the activation energy to the subcutaneous port through a second plurality of electrodes, and a plurality of electrical interconnections to establish electrical communication between the first plurality of electrodes of the subcutaneous connector and respective ones of the second plurality of electrodes of the transcutaneous connector.

These and other objects and features of the present disclosure will become more fully apparent from the following description and appended claims, or may be learned by the practice of the embodiments as set forth.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the disclosure's scope, the embodiments will be described and explained with specificity and detail in reference to the accompanying drawings.

DETAILED DESCRIPTION OF THE PREFERRED EMBODIMENTS

Figure 1:
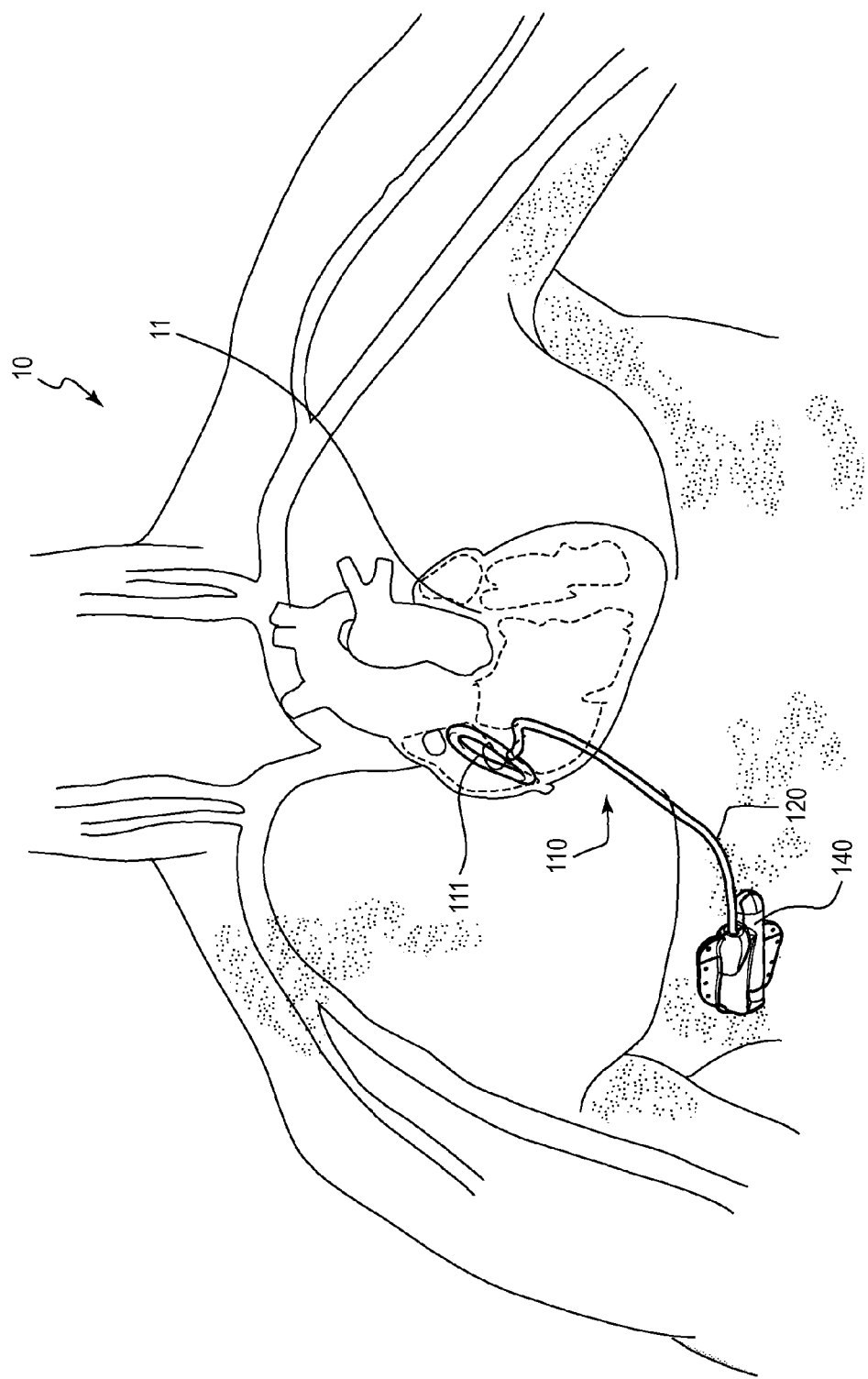
FIG. 1 is a perspective view of one embodiment of an annuloplasty ring assembly, after the ring assembly has been placed in a patient's body.

The present disclosure describes providing activation energy to an adjustable annuloplasty ring during implantation and/or over the course of a patient's lifetime. In certain embodiments, an adjustable annuloplasty ring is implanted into the body of a patient such as a human or other animal. The adjustable annuloplasty ring is implanted through an incision or body opening either thoracically (e.g., open-heart surgery) or percutaneously (e.g., via a femoral artery or vein, or other arteries or veins) as is known to someone skilled in the art. The adjustable annuloplasty ring is attached to the annulus of a heart valve to improve leaflet coaptation and to reduce regurgitation. The annuloplasty ring may be selected from one or more shapes comprising a round or circular shape, an oval shape, a C-shape, a D-shape, a U-shape, an open circle shape, an open oval shape, and other curvilinear shapes.

The size of the annuloplasty ring can be adjusted postoperatively to compensate for changes in the size of the heart. As used herein, "postoperatively" refers to a time after implanting the adjustable annuloplasty ring and closing the body opening through which the adjustable annuloplasty ring was introduced into the patient's body. For example, the annuloplasty ring may be implanted in a child whose heart grows as the child gets older. Thus, the size of the annuloplasty ring may need to be increased. As another example, the size of an enlarged heart may start to return to its normal size after an annuloplasty ring is implanted. Thus, the size of the annuloplasty ring may need to be decreased postoperatively to continue to reinforce the heart valve annulus.

In some embodiments, the annuloplasty ring comprises a shape memory material that is responsive to changes in temperature and/or exposure to a magnetic field. Shape memory is the ability of a material to regain its shape after deformation. Shape memory materials include polymers, metals, metal alloys and ferromagnetic alloys. The annuloplasty ring is adjusted in vivo by applying an energy source to activate the shape memory material and cause it to change to a memorized shape.

In the example embodiments described herein, the energy source provides radio frequency (RF) energy to the shape memory material through a subcutaneous port or connector. Persons skilled in the art will recognize, however, that the described embodiments may be adapted to provide other types of energy to activate the shape memory material within the annuloplasty ring including, for example, x-ray energy, microwave energy, ultrasonic energy such as focused ultrasound, high intensity focused ultrasound (HIFU) energy, light energy, electrical energy, magnetic field energy, thermal energy, other types of energy, and combinations of the foregoing. For example, one embodiment of electromagnetic radiation that is useful in infrared energy having a wavelength in a range between approximately 750 nanometers and approximately 1600 nanometers. This type of infrared radiation may be produced efficiently by a solid state diode laser. In certain embodiments, the annuloplasty ring implant is selectively heated using short pulses of energy having an on and off period between each cycle. The energy pulses provide segmental heating which allows segmental adjustment of portions of the annuloplasty ring without adjusting the entire implant.

In certain example embodiments, an adjustable annuloplasty system includes an internal assembly and an external assembly. The internal assembly may be referred to herein as an annuloplasty ring assembly and may include an adjustable annuloplasty ring, a subcutaneous activation cable coupled to the adjustable annuloplasty ring, a subcutaneous connector coupled to the subcutaneous activation cable, and a subcutaneous port configured to be coupled to the subcutaneous connector. The external assembly may be referred to herein as an adjustment assembly and may include an RF generator, a transcutaneous activation cable coupled to the RF generator, and a transcutaneous connector coupled to the transcutaneous cable. Adjustments may be made to the annuloplasty ring by coupling the transcutaneous connector to the subcutaneous port. In some embodiments, this may require that a small incision be made in the patient's skin. Once coupled to the annuloplasty ring through the respective cables and the subcutaneous port, energy from the RF generator may be used to change the shape and/or dimensions of the adjustable annuloplasty ring.

In another example embodiment, the internal assembly does not include the subcutaneous port. Rather, the subcutaneous connector may be covered with a protective cap and implanted under the patient's skin until it is ready to be used. To provide activation energy to the adjustable annuloplasty ring implanted in the patient's heart, an incision may be made in the patient's skin through which the subcutaneous connector may be pulled from the patient's body and coupled directly to the RF generator or an external activation cable.

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the disclosure, as claimed, but is merely representative of various embodiments. While the various aspects of the embodiments are presented in drawings, the drawings are not necessarily drawn to scale unless specifically indicated.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other.

FIG. 1 is a perspective view of an embodiment of an annuloplasty ring assembly 110, which may comprise an internal portion of an adjustable annuloplasty system. Annuloplasty ring assembly 110 may comprise an adjustable annuloplasty ring 111, a subcutaneous activation cable 120, and a subcutaneous port 140. In FIG. 1, annuloplasty ring assembly 110 has been implanted in a heart 11 of a patient 10. In the depicted embodiment, adjustable annuloplasty ring 111 has been implanted around the annulus of the mitral valve of heart 11; however, in alternative embodiments, the adjustable annuloplasty ring 111 may be implanted in a tricuspid valve or other heart valve. Subcutaneous activation cable 120 may attach to adjustable annuloplasty ring 111 at or near a $P_3/P_2$ region of the mitral valve to facilitate passing the subcutaneous activation cable 120 through an incision in a wall of the myocardium. Subcutaneous activation cable 120 may be routed up and over the right atrial appendage (RAA), and down to the abdominal area below the diaphragm. Subcutaneous port 140 may be anchored to subcutaneous tissue to limit migration of the port.

Figure 2:
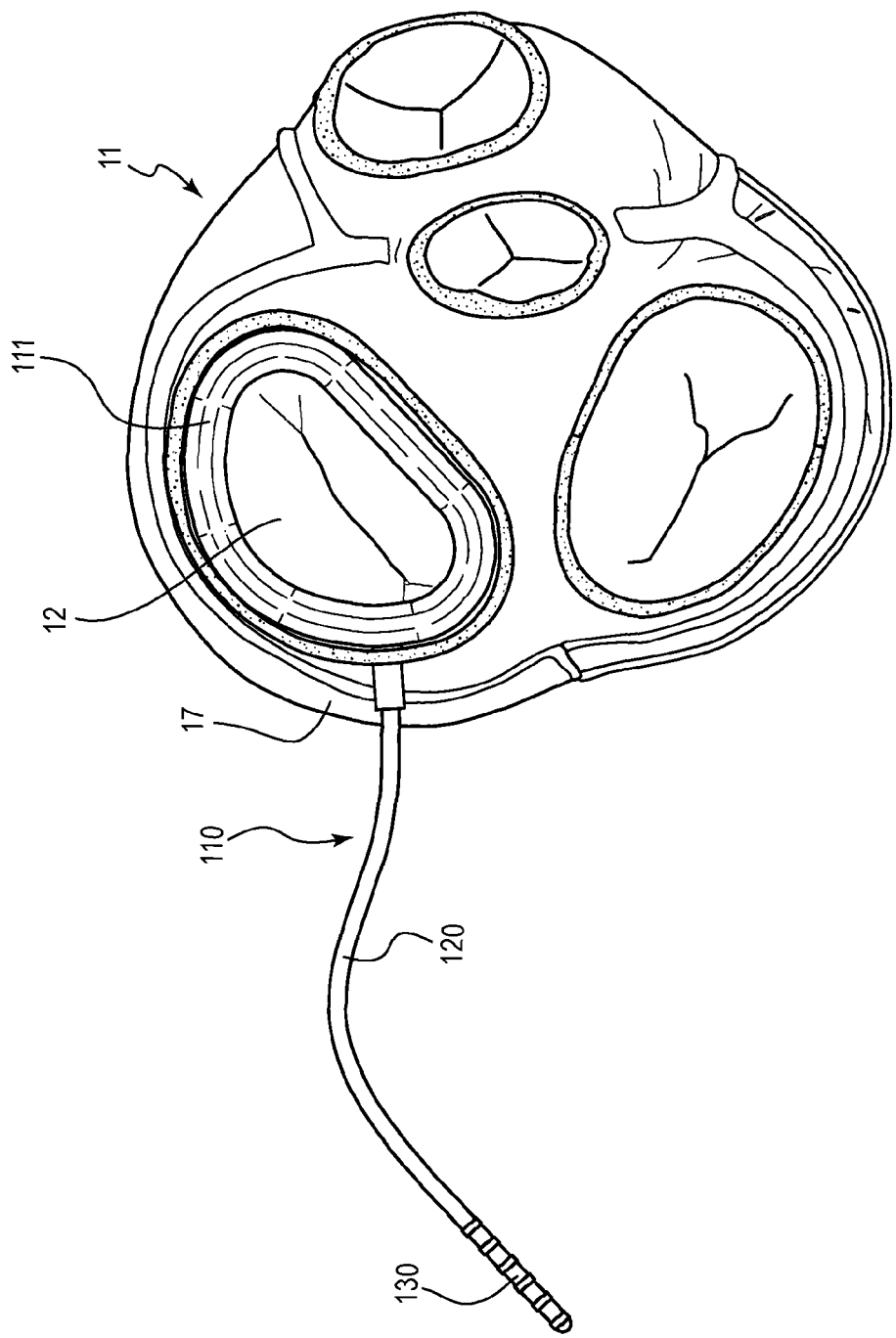
FIG. 2 is a cutaway view of a patient's heart, in which an annuloplasty ring has been placed according to one embodiment.

FIG. 2 is a cutaway view of heart 11 with adjustable annuloplasty ring 111 implanted around the annulus of the mitral valve 12. Subcutaneous activation cable 120 may exit myocardial wall 17 in proximity to the coronary sinus such that the routing avoids major arteries and veins. Subcutaneous activation cable 120 may comprise a flexible cable to achieve an optimal routing for each patient. Subcutaneous activation cable 120 may be configured to exit the heart 11 at a location near the P2/P1 leaflet junction of the mitral valve 12. Subcutaneous activation cable 120 may terminate in a connector, such as subcutaneous connector 130, which comprises a six electrode in-line connector. One skilled in the art will recognize that a variety of types and configurations of cables and connectors may be employed without departing from the spirit of this disclosure. For example, the subcutaneous connector may not comprise an in-line connector and may comprise any suitable number of electrodes.

Figure 3:
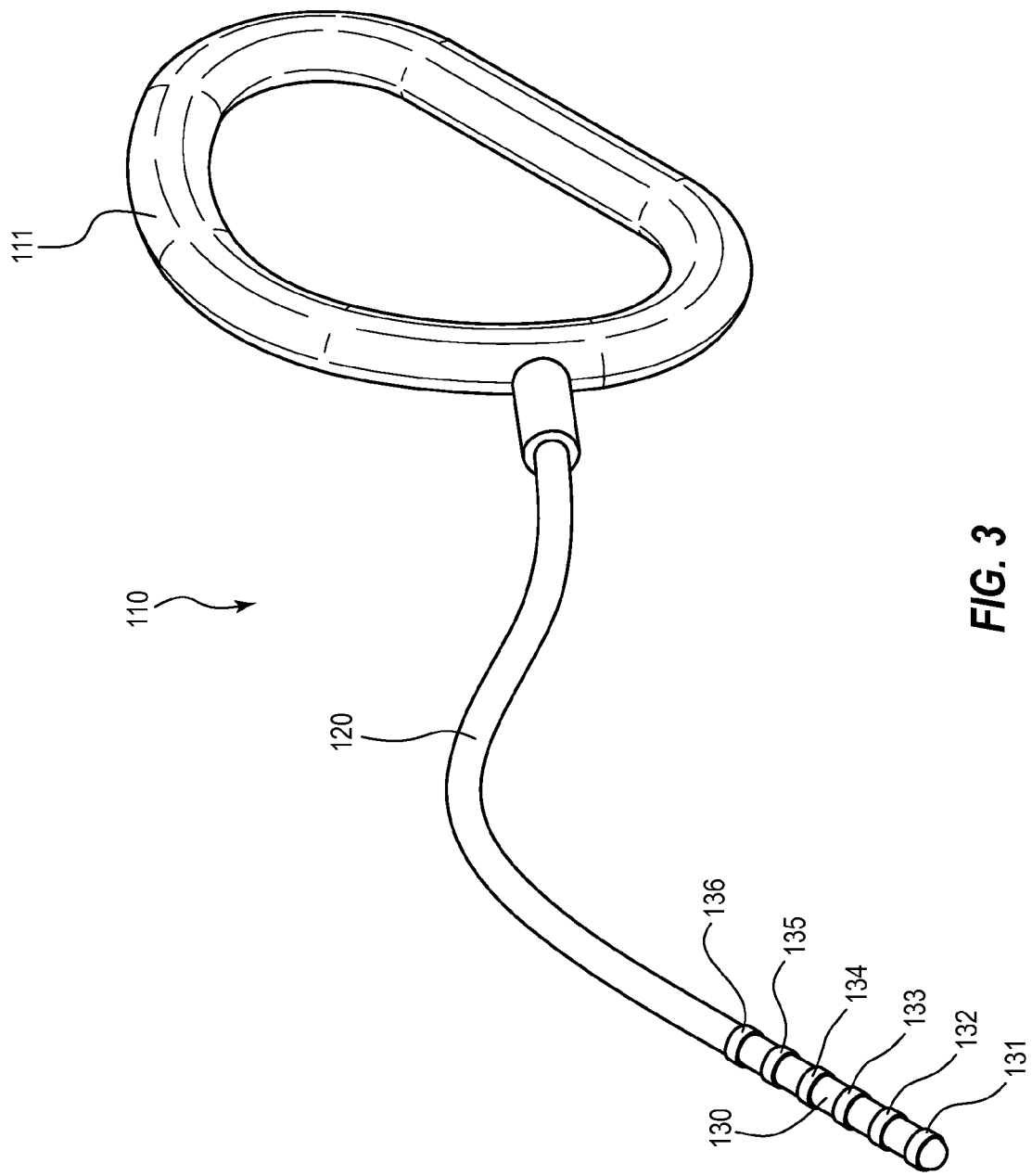
FIG. 3 is a perspective view of a portion of the annuloplasty ring assembly shown in FIG. 1.

FIG. 3 is a perspective view of annuloplasty ring assembly 110. As described herein, adjustable annuloplasty ring 111 is coupled to subcutaneous activation cable 120, which terminates with subcutaneous connector 130. Subcutaneous connector 130 comprises an in-line six electrode (or lead) connector. Subcutaneous connector 130 comprises a first electrode 131, a second electrode 132, a third electrode 133, a fourth electrode 134, a fifth electrode 135, and a sixth electrode 136. In an example embodiment, first through sixth electrodes 131-136 provide the following functions: first electrode 131: an RF signal (RF+) for RF activation; second electrode 132: a return RF signal (RF−) for RF activation; third electrode 133: a thermocouple signal (TC+) for temperature measurement; fourth electrode 134: return thermocouple signal (TC−) for temperature measurement; fifth electrode 135: identification signal (ID+) for ring recognition resistor; and sixth electrode 136: return identification signal (ID−) for ring recognition resistor. Such functions are described in detail below with respect to FIG. 12. One skilled in the art will recognize that a variety of functions can be assigned to the various electrodes of the subcutaneous connector 130. For example, more than one thermocouple may be used and/or the order of the particular functions assigned to particular electrodes may be rearranged. Further, the subcutaneous connector 130 may have as few as one electrode or many more than six electrodes.

Figure 4:
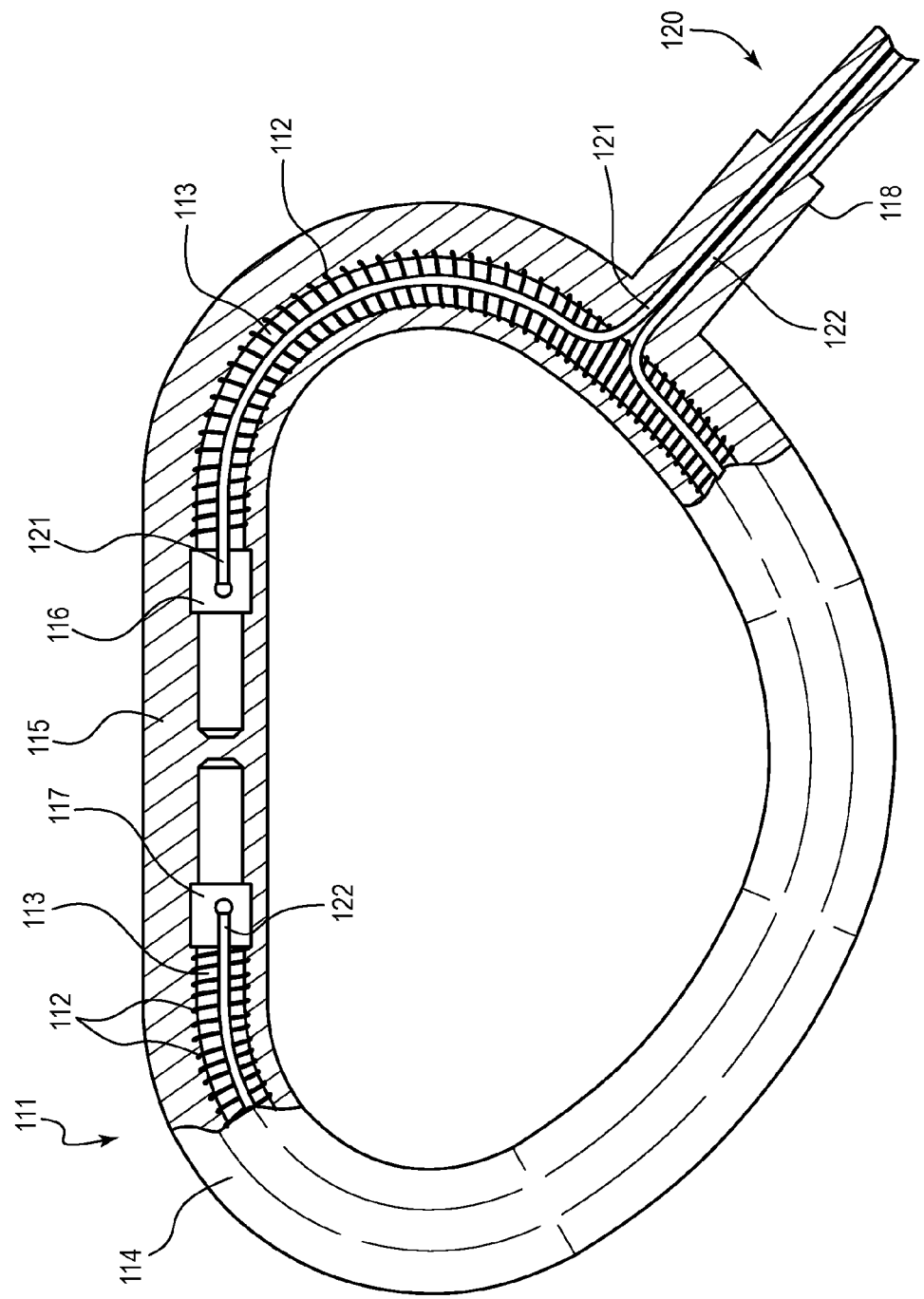
FIG. 4 is a cutaway view of the annuloplasty ring of FIG. 3.

FIG. 4 depicts a cutaway view of adjustable annuloplasty ring 111 and subcutaneous activation cable 120 according to one embodiment. Adjustable annuloplasty ring 111 includes a shape memory core 113 that is wrapped by a heating element 112. A first end of heating element 112 is coupled to a first electrode 116 and a second end of heating element 112 is coupled to a second electrode 117. Heating element 112 may comprise one or more wires configured as a coil. Heating element 112 generates heat when RF energy passes through the coil. Heating element 112 transfers the generated heat to the shape memory core 113 for changing the shape of the adjustable annuloplasty ring 111.

In this example embodiment, subcutaneous activation cable 120 is coupled to the adjustable annuloplasty ring 111 through a silicone strain relief 118. As shown in FIG. 4, subcutaneous activation cable 120 includes a first RF lead 121 coupled to the first electrode 116 and a second RF lead 122 coupled to the second electrode 117. First RF lead 121 and second RF lead 122 extend through subcutaneous activation cable 120 to subcutaneous connector 130 (shown in FIGS. 2 and 3) for receiving RF energy from the RF generator (e.g., through the subcutaneous port 140).

Although not shown in FIG. 4 for clarity, and as described elsewhere herein, subcutaneous activation cable 120 may include other leads or elements for measuring the temperature of the heating element 112 and/or shape memory core 113, and/or for uniquely identifying the particular adjustable annuloplasty ring 111. For example, one or more thermocouples may extend from subcutaneous activation cable 120 so as to be located proximate the heating element 112 and/or the shape memory core 113. As another example, subcutaneous activation cable 120 may include a resistor having a unique value associated with the adjustable annuloplasty ring 111 to which subcutaneous activation cable 120 is attached. In an alternative embodiment, such a resistor may by located within adjustable annuloplasty ring 111 and may be selectively coupled to resistance measuring equipment located external to the patient through a corresponding lead in subcutaneous activation cable 120.

As shown in FIG. 4, a casing 115 may envelope the above components, and a sheath 114 may at least partially encapsulate casing 115. Casing 115 may comprise a flexible material such as silicone rubber. The sheath may comprise a suturable material such as woven polyester cloth, Dacron®, woven velour, polyurethane, polytetrafluoroethylene (PTFE), heparin-coated fabric, or other biocompatible material. In some embodiments, the suturable material comprises a biological material such as bovine or equine pericardium, homograft, patient graft, or cell-seeded tissue.

In certain embodiments, sheath 114 may be marked with a safety suture line (not shown), which may be sewn or otherwise marked as a continuous midline at about 1.5 mm from an outer edge of adjustable annuloplasty ring 111. The safety suture line establishes an edge of the heating element coils 112 such that a suturing needle does not contact the heating element coils while adjustable annuloplasty ring 111 is sewn to a heart valve annulus.

Figure 5:
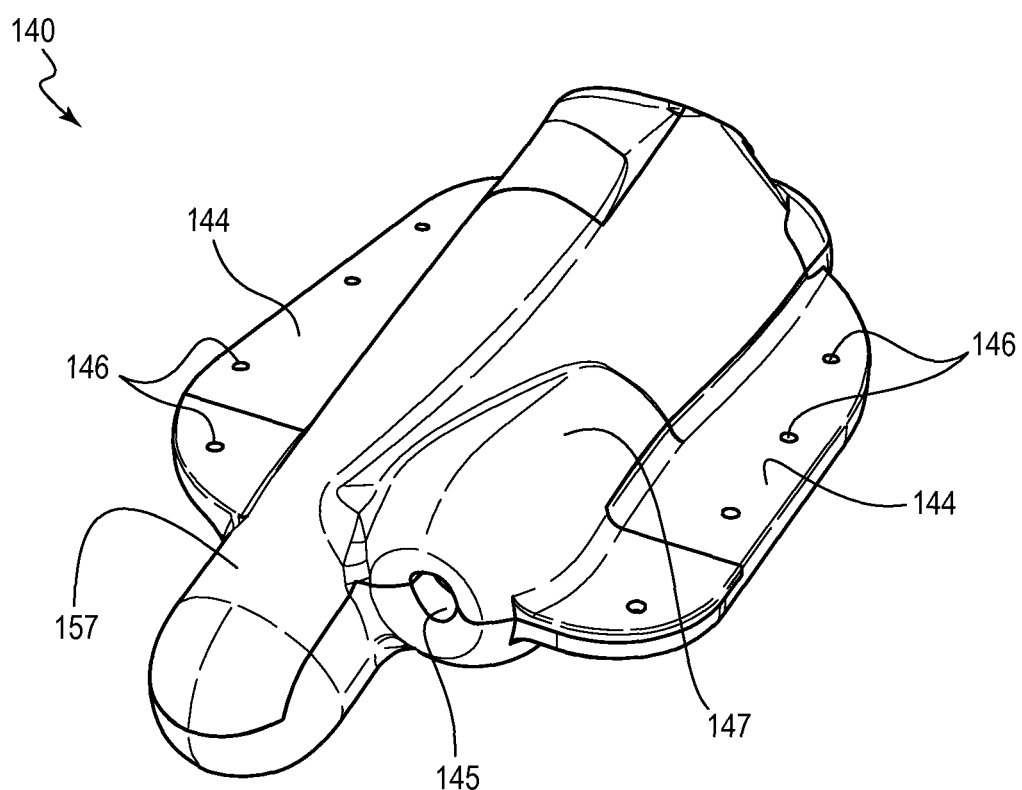
FIG. 5 is a perspective view of a port according to one embodiment.

FIG. 5 depicts a perspective view of subcutaneous port 140 according to one embodiment. As shown, subcutaneous port 140 may comprise flanges 144, ring connector aperture 145, suture apertures 146 in flanges 144, ring connector port 147, and instrument port 157. Subcutaneous port 140 is configured to allow an electronic instrument located outside a patient's body to communicate with an adjustable annuloplasty ring, which may be located inside a patient's body. Subcutaneous port 140 may comprise one or more pieces of one or more biocompatible materials. Subcutaneous port 140 may comprise a rigid or semi-rigid member, and may comprise, for example, polycarbonate, acrylonitrile butadiene styrene (ABS), and/or polysulfone. Flanges 144 and suture apertures 146 allow subcutaneous port 140 to be positioned and retained in a selected location and orientation within a patient's body. Ring connector aperture 145 is configured to receive subcutaneous connector 130 of annuloplasty ring assembly 110 (shown in FIG. 3).

Figure 6:
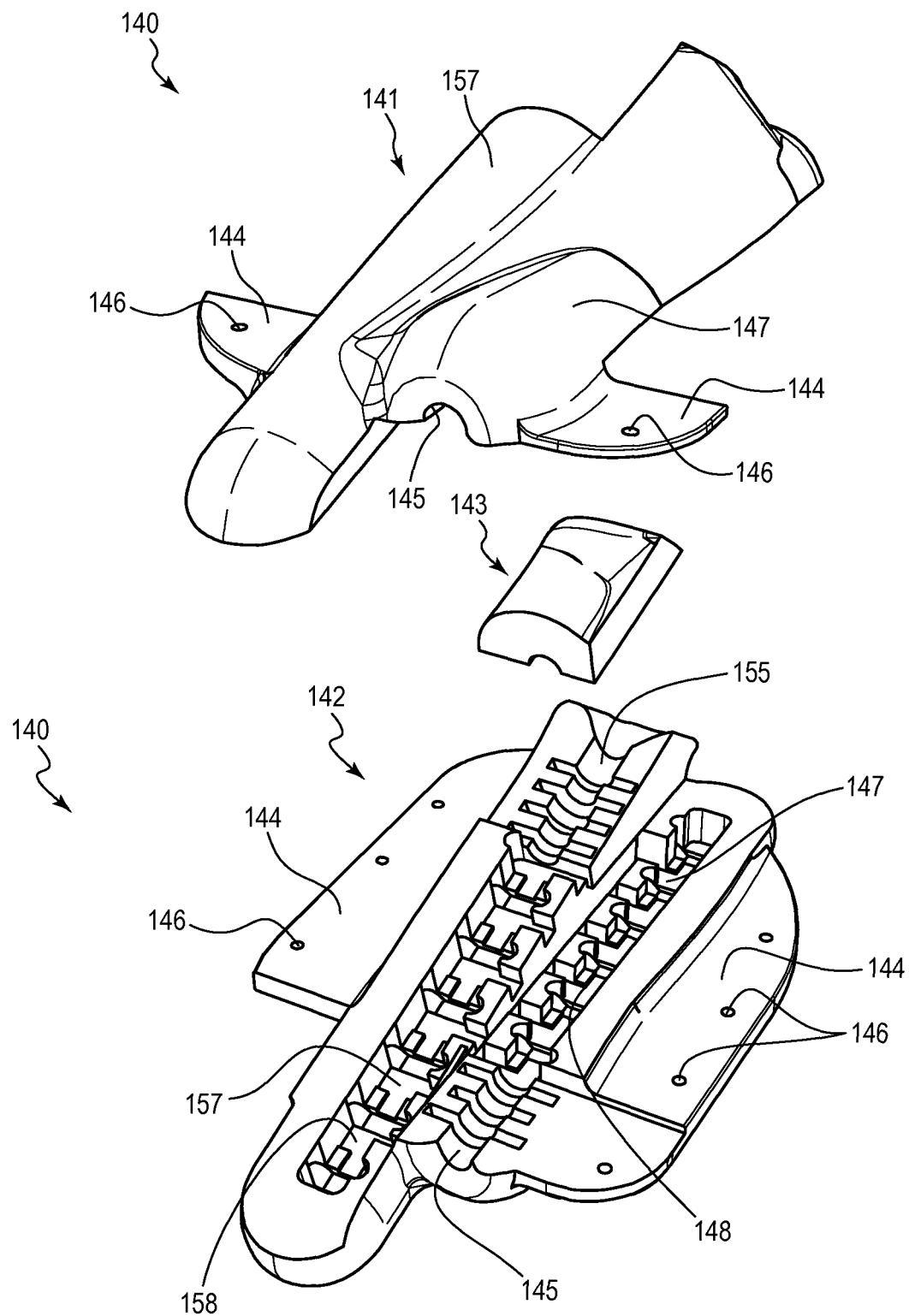
FIG. 6 is an exploded perspective view of the port of FIG. 5.

FIG. 6 is an exploded perspective view of components of subcutaneous port 140. For illustrative purposes, certain components such as o-rings (see FIGS. 11A, 11B, and 11C) and electrical interconnections between channels (see FIGS. 8 and 9) are not shown in FIG. 6. Subcutaneous port 140 may comprise a first portion 141, a second portion 142, and a third portion 143. The three portions 141, 142, 143 provide ease in manufacturing. Skilled persons will recognize, however, that the present disclosure is not so limited and that the subcutaneous port 140 in certain embodiments may include a single piece, two pieces (e.g., third portion 143 may simple be part of first portion 141), or more than three pieces.

In the depicted embodiment, first, second and third portions 141, 142, and 143 may individually comprise portions of all, or some of, the structures of subcutaneous port 140. First portion 141 and second portion 142 comprise portions of suture apertures 146. First portion 144 also comprises a portion of flanges 144, suture apertures 146, ring connector insert aperture 145, ring connector port 147, ring connector channel 148, instrument connector aperture 155, instrument port 157, and instrument channel 158.

Second portion 142 and third portion 143 cooperate to secure o-rings (not shown) in respective slots (four shown) at instrument connector aperture 155. At least one of the o-rings at the instrument connector aperture 155 may comprise a pre-scored membrane that keeps fluids from entering subcutaneous port 140. Similarly, first portion 141 and second portion 142 cooperate to secure o-rings (not shown) in respective slots (four shown) at ring connector insert aperture 145. During use, The o-rings at both ports 145, 155 interface with male connectors (or other devices such as trocars or cannulas) inserted therein to prevent fluids from entering the subcutaneous port 140. Before being introduced into a patient's body, one or both apertures 145 and 155 may be sealed such that the apertures are water-tight. The apertures may be sealed using, for example, adhesive silicone, silicone tape, or a silicone membrane.

Figure 7:
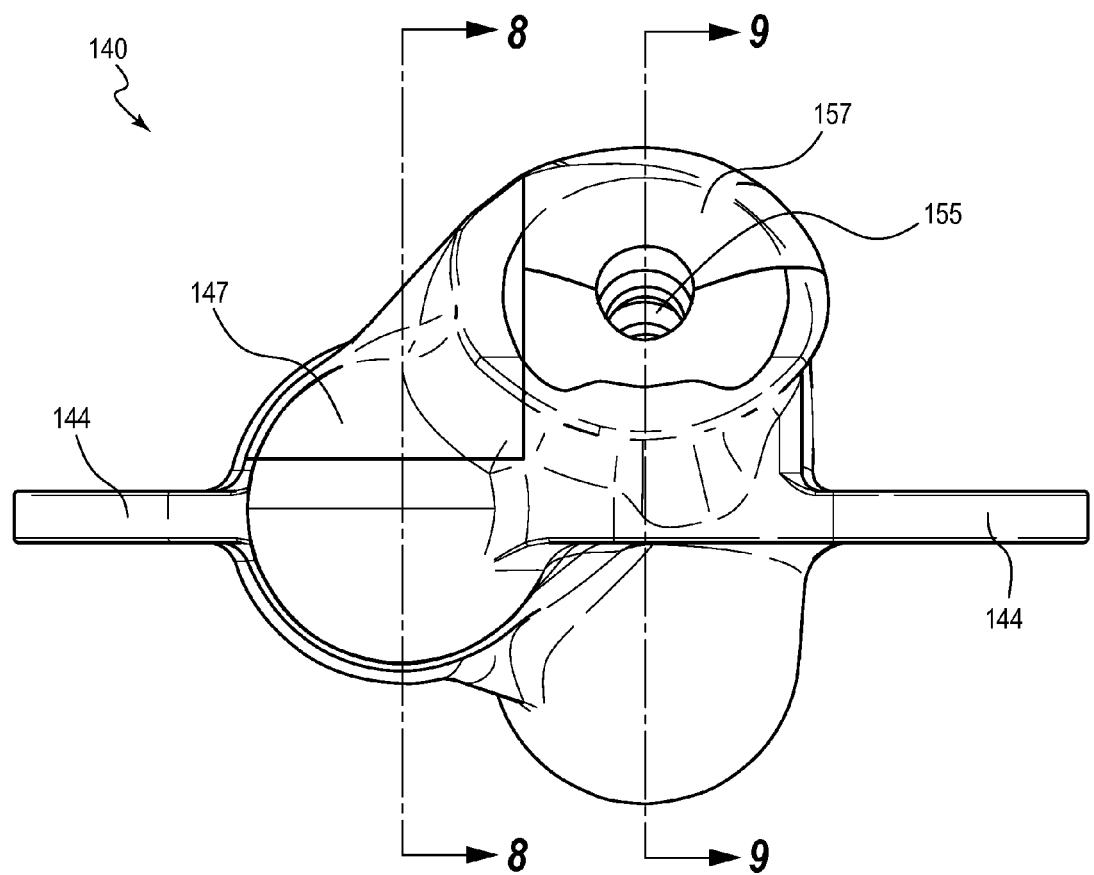
FIG. 7 is an end view of an instrument side the port of FIG. 5.

FIG. 7 is a close up end view of an instrument side of subcutaneous port 140. Flanges 144 comprise substantially planar protrusions of subcutaneous port 140. An instrument aperture 155 allows an instrument connector to be inserted into instrument port 157. Instrument port 157 is located adjacent to ring port 147, and the two ports are configured to allow electronic communication between each other via a series of electronic connectors.

Figure 8:
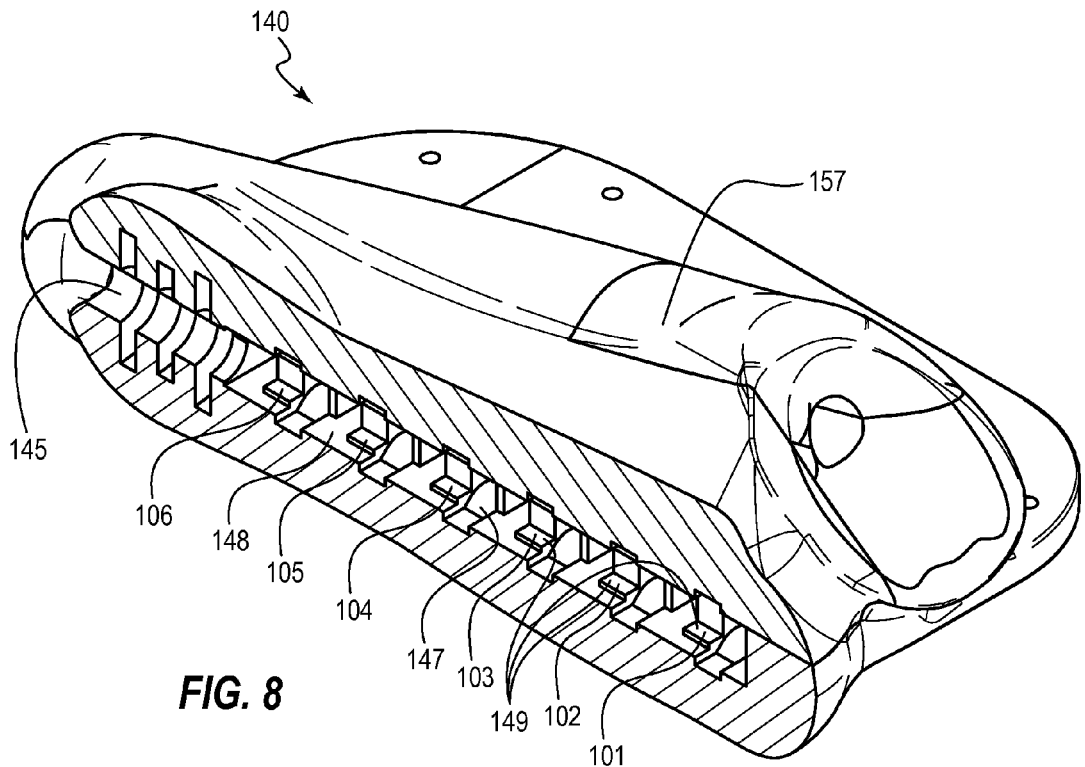
FIG. 8 is a longitudinal cross-sectional view of a portion of the port of FIG. 5.
Figure 9:
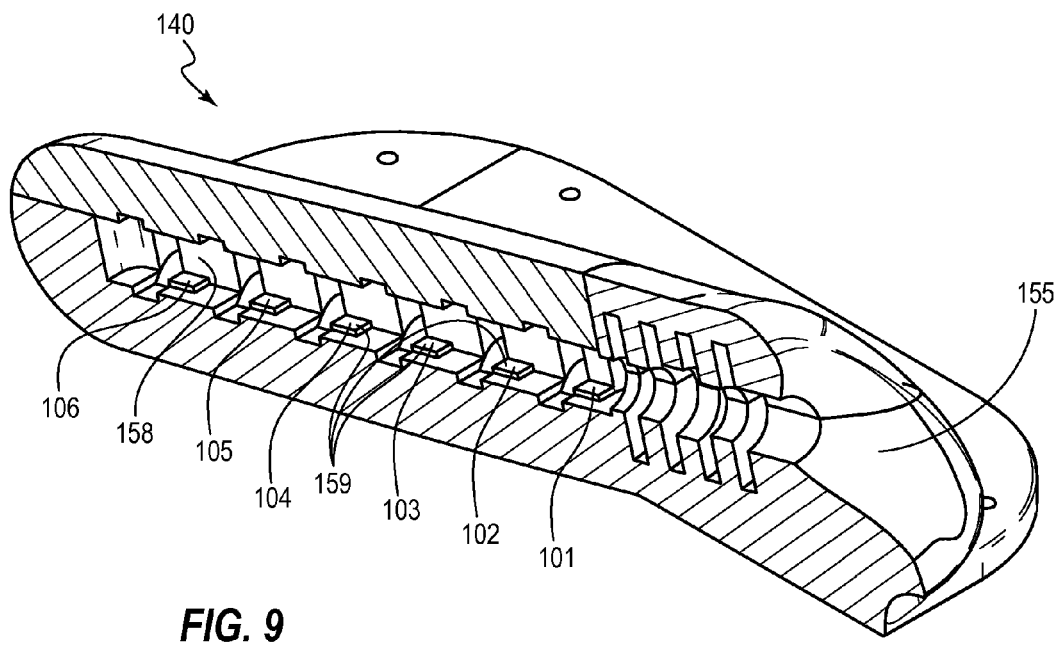
FIG. 9 is a longitudinal cross-sectional view of another portion of the port of FIG. 5.

FIGS. 8-9 are longitudinal cross-sectional views of subcutaneous port 140, wherein FIG. 8 is a cross-section of ring connector port 147 and FIG. 9 is a cross-section of instrument connector port 157. In FIGS. 8-9, subcutaneous port 140 is in the same orientation; however a depth of the longitudinal cross-section is altered between the figures. FIG. 8 depicts a longitudinal cross-section of ring connector port 147, which may comprise ring connector insert aperture 145 and a ring connector channel 148. Ring connector channel 148 comprises a set of electronic connectors that extend across subcutaneous port 140 to instrument connector port 157. The electronic connectors comprise a first electronic connector 101, a second electronic connector 102, a third electronic connector 103, a fourth electronic connector 104, a fifth electronic connector 105, and a sixth electronic connector 106. Only first portions 149 of electronic connectors 101-106 are located in ring port 147, as the connectors extend across port 147 and protrude into instrument port 157. Port 147 is adjacent to, but oppositely oriented from port 157. Likewise, ring connector aperture 145 opposes aperture 155.

FIG. 9 is a longitudinal cross-sectional view of instrument port 157, which may comprise instrument connector insert aperture 155 and an instrument connector channel 158. Channel 158 may comprise second portions 159 of electrical connectors 101-106 that are opposite to the sides of the electrical connectors that are located in channel 148, as depicted in FIG. 8. As shown in FIGS. 8 and 9, an axis of channel 148 is in a first plane, an axis of channel 158 is in a second plane, and the first plane is parallel to the second plane. In other words, channels 148 and 158 run next to each other to reduce the overall size of subcutaneous port 140. The axis of channel 148 is also at an angle with respect to an axis of channel 158 such that implanting subcutaneous port 140 within subcutaneous tissue of the patient with the axis of channel 148 pointing substantially parallel to a surface of the patient's skin results in the axis of channel 158 pointing, at an angle with respect to the surface of the patient's skin, toward the surface of patient's skin to thereby provide access to aperture 155 through a trocar or needle from the surface of the patient's skin. In other words, instrument connector port 157 is slanted at an angle with respect to flanges 144 and/or ring connector port 147. Further, the entrance to instrument connector port 157 includes a large slanted target area that funnels into instrument aperture 155. Thus, a surgeon or other practitioner may easily insert a trocar or cannulated needle through the patient's skin into the instrument connector port 157.

Electronic connectors 101-106 may comprise any suitable electrical conductor. For example the electronic connectors may comprise stainless steel 304. In another embodiment, the connectors may comprise conductive silicone, which may comprise gold or silver impregnated silicone. Since ring connector port 147 and instrument connector port 157 are configured in opposing orientations, in embodiments where electronic connectors 101-106 extend straight across subcutaneous port 140, an order of electrodes on subcutaneous connector 130 (shown in FIG. 3) may be reversed compared to an order of electrodes on instrument connector 160 (shown in FIG. 11C). However, in embodiments where the electronic connectors cross each other, the order of electrodes on the ring connector may not be reversed compared to the instrument connector.

Figure 10:
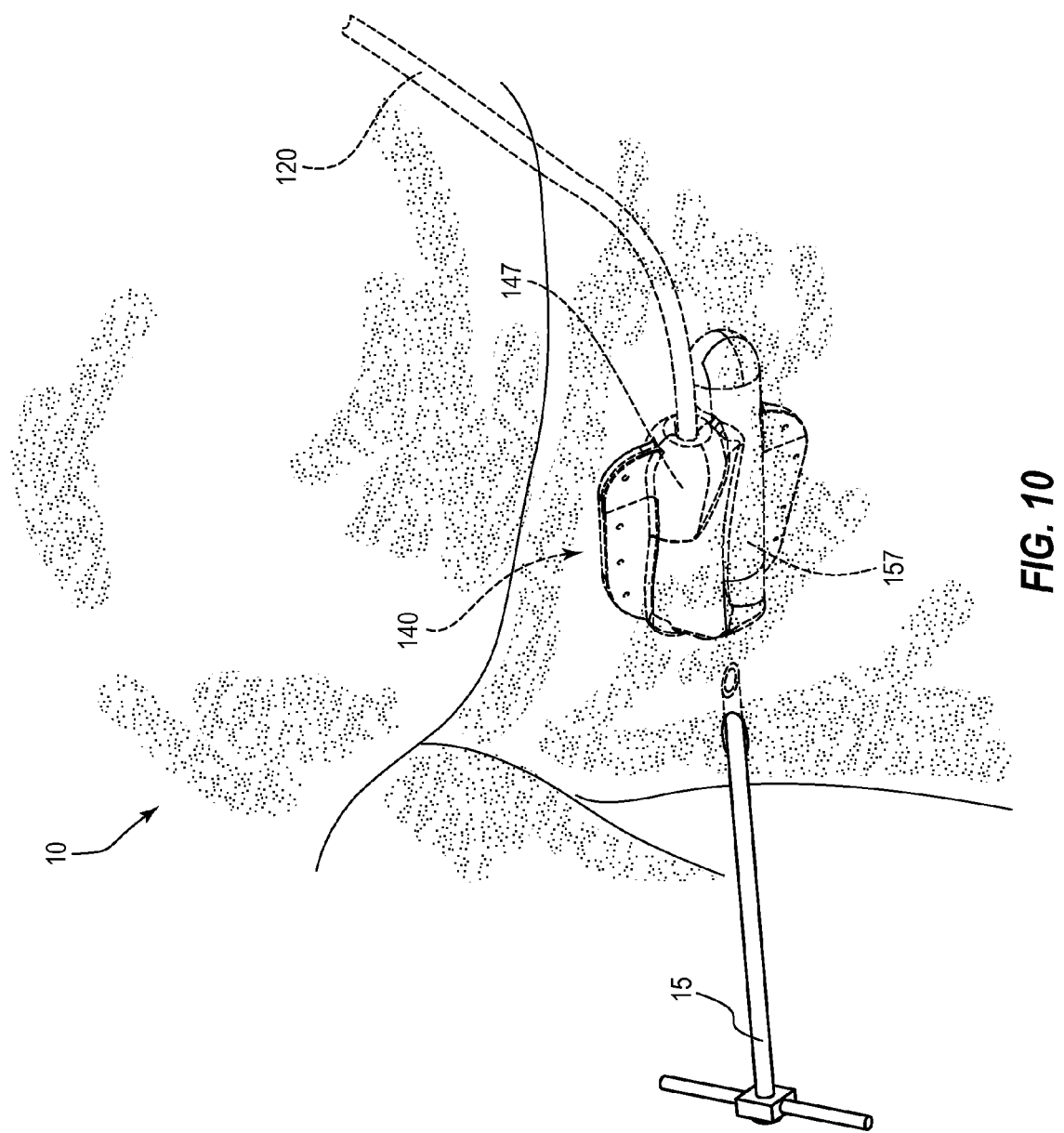
FIG. 10 is a perspective view of an instrument gaining access to the port according to one embodiment.
Figure 11A:
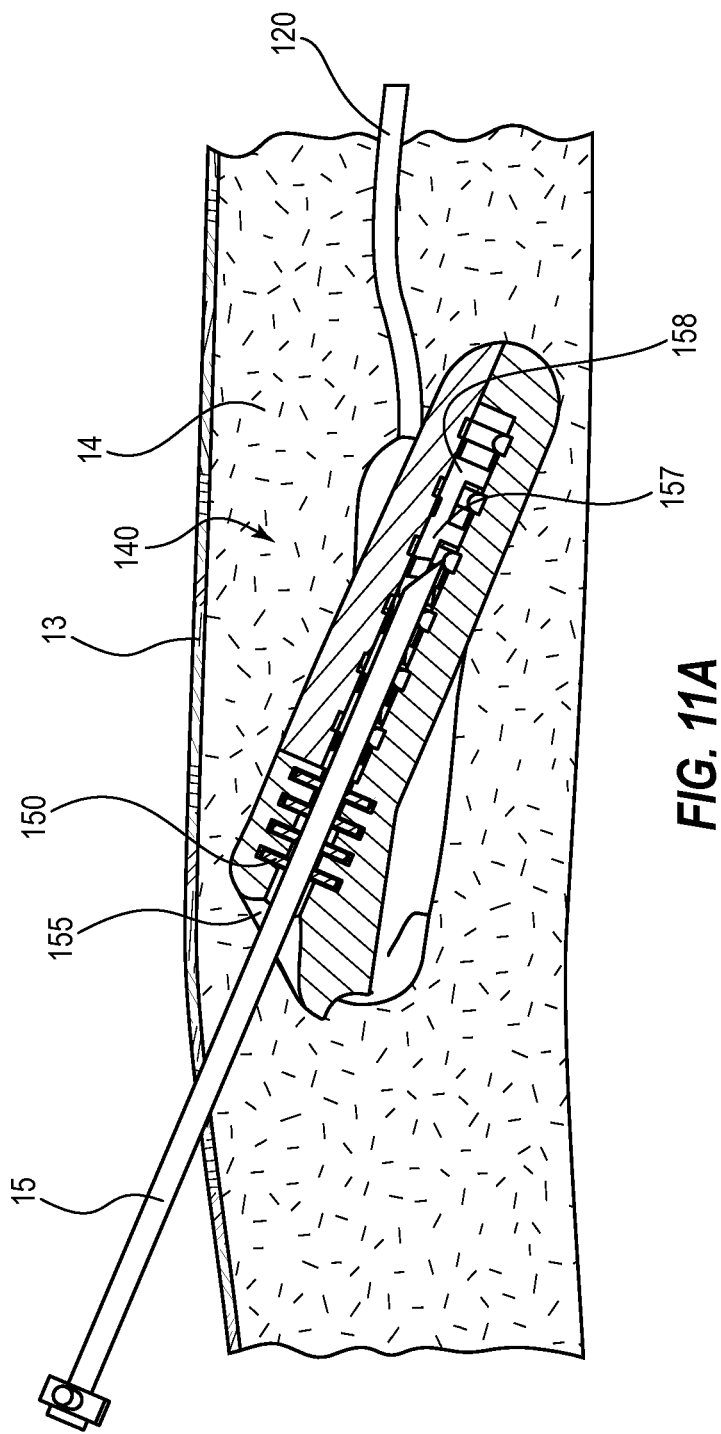
FIG. 11A is a cross sectional view of an instrument gaining access to the port according to one embodiment.
Figure 11B:
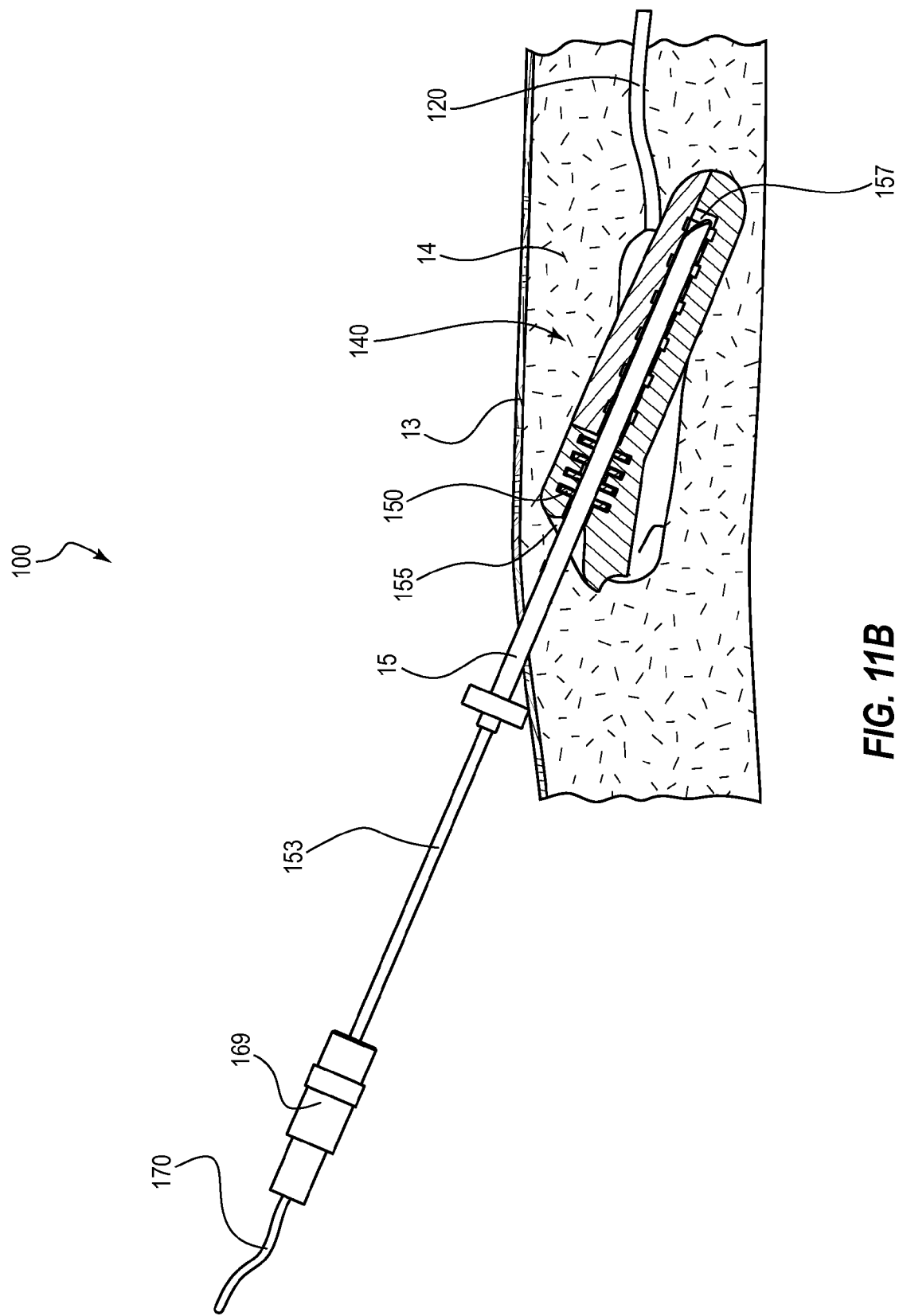
FIG. 11B is a cross sectional view of an instrument gaining access to the port according to one embodiment.
Figure 11C:
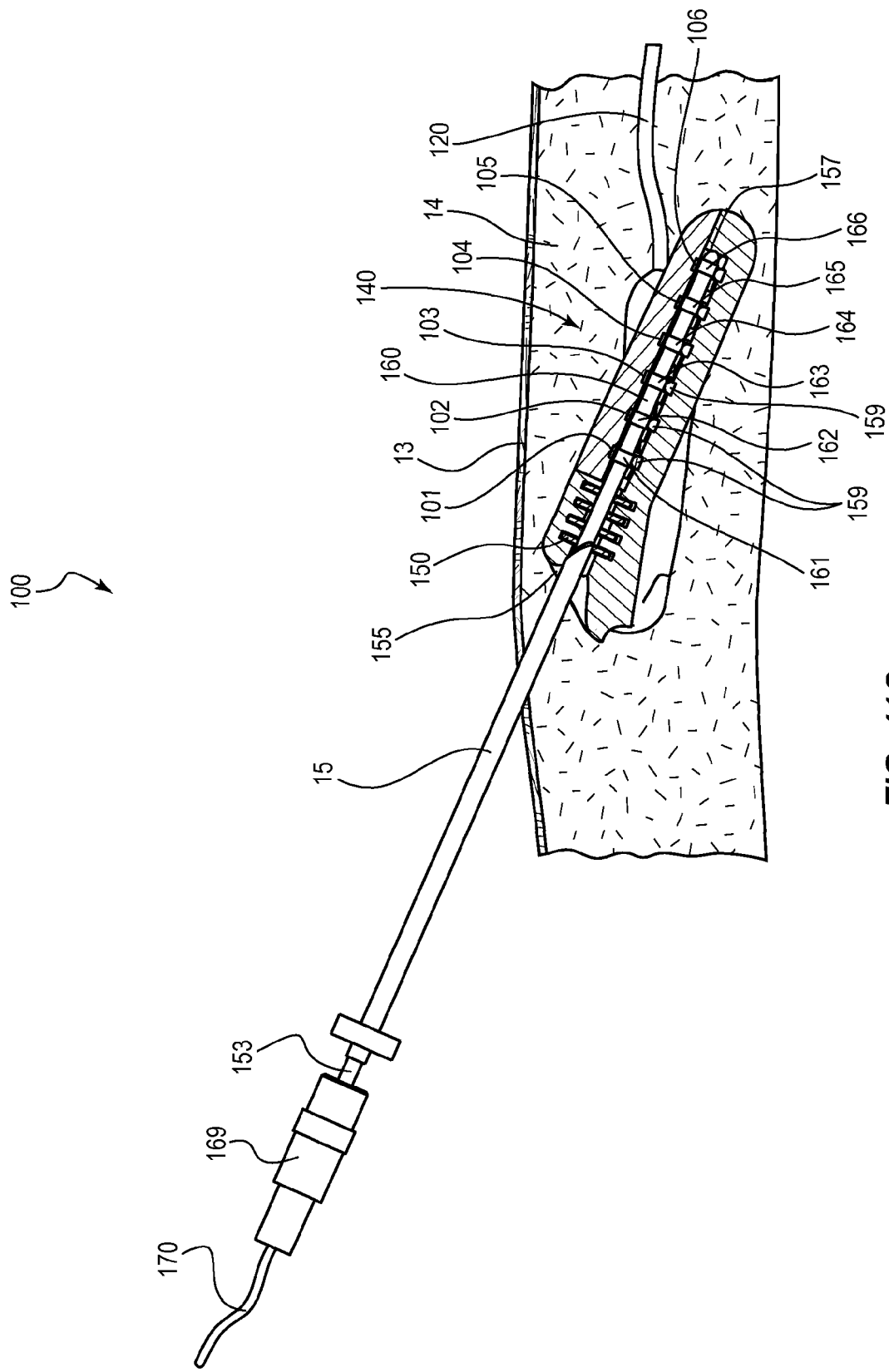
FIG. 11C is a cross sectional view of an instrument gaining access to the port according to one embodiment.

FIGS. 10-11C illustrate various views of subcutaneous port 140 implanted under a patient's skin and may depict a method for connecting an instrument to an annuloplasty ring. The figures may also be described as depicting a method for adjusting (or synching) an in vivo annuloplasty ring.

FIG. 10 is a perspective view of subcutaneous port 140 that has been placed under the skin of patient 10. Subcutaneous port 140 is coupled to an annuloplasty ring (such as adjustable annuloplasty ring 111 shown in FIGS. 1-4) via subcutaneous activation cable 120. Subcutaneous activation cable 120 may comprise a connector (such as subcutaneous connector 130 shown in FIGS. 2 and 3) that was previously inserted by a surgeon into ring connector port 147. As illustrated, a trocar 15 pierces the skin of patient 10 and is in alignment with instrument port 157 of subcutaneous port 140. The aperture of instrument port 157 may sealed closed by a cap, tape, membrane, or plug, which may require removal by the surgeon before the trocar can be introduced into the instrument port. In other embodiments, the surgeon may puncture through such a seal with trocar 15. One skilled in the art will recognize that a variety of instruments and techniques may be employed to align and/or insert an instrument connector with a subcutaneous instrument connector port (157 in FIG. 10) without departing from the spirit of the present disclosure. For example, a needle or cannula may be used with, or instead of, the trocar.

FIGS. 11A, 11B, and 11C are cross-sectional views of subcutaneous port 140 that is located in subcutaneous tissue 14 of a patient. Instrument connector port 157 is oriented upwardly toward the patient's skin 13 so that an instrument, such as trocar 15 may be introduced through the skin and into chamber 158 of instrument connector port 157 via aperture 155. Subcutaneous port 140 is in electronic communication with the adjustable annuloplasty ring via subcutaneous activation cable 120. Trocar 15 may not be fully inserted into chamber 158 of port 157, as depicted in FIGS. 11A-11B; rather, in some embodiments, the trocar may only be slightly inserted into chamber 158 in a region corresponding to o-rings 150 (four shown). One or more of the o-rings 150 (e.g., the o-ring 150 at instrument aperture 155) may comprise a gasket or silicone membrane to prevent fluids from entering chamber 158. During insertion, trocar 15 may puncture through the gasket or silicone membrane and form a seal with one or more of the plurality of o-rings 150 to further prevent entry of fluid during use. After trocar 15 is aligned with insert aperture 155 of port 157, an instrument connector 160 (shown in FIG. 11C and also referred to herein as a transcutaneous connector) at a distal end of a transcutaneous activation cable 153 may be introduced into trocar 15. A proximal end of transcutaneous activation cable 153 may have an instrument plug 169 that couples a cable 170 of the instrument (e.g., RF generator) to transcutaneous activation cable 153.

FIG. 11C depicts instrument connector 160 after trocar 15 has at least been partially withdrawn such that the instrument connector 160 has been fully inserted into instrument port 157 and has been seated such that connector electrodes 161, 162, 163, 164, 166 of instrument connector 160 are in electronic communication with instrument port portions 159 of electronic connectors 101-106. In other embodiments, trocar 15 is fully removed and transcutaneous activation cable 153 and/or instrument connector 160 form a seal with the o-rings 150.

The configuration of FIG. 11C allows an external energy source, such as an RF generator to transmit energy through subcutaneous port 140 to heating elements of the annuloplasty ring. As described above, the heating elements may transmit heat to the shape memory core of the annuloplasty ring, thereby causing at least one of the dimensions of the ring to be altered. As such, the annuloplasty rings of this disclosure may be characterized as adjustable annuloplasty rings. After a selected amount of adjustment is made to the annuloplasty ring, instrument connector 160 and trocar 15 may be removed from the patient and aperture 155 of instrument connector port 157 may be re-sealed using a cap, plug, or tape.

Figure 12:
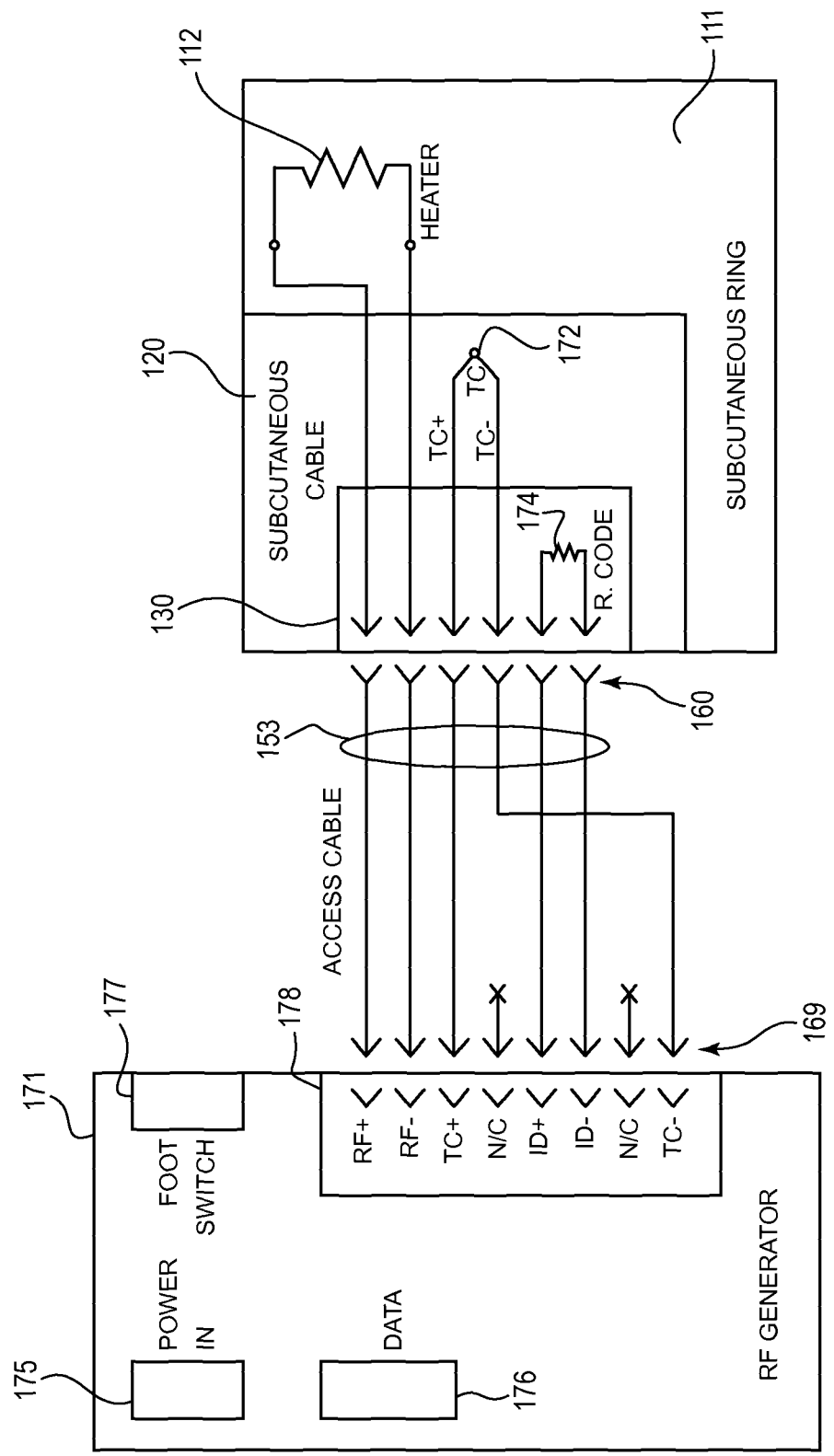
FIG. 12 is a schematic diagram of the wiring of the annuloplasty ring and adjustment assembly according to one embodiment.

FIG. 12 is a schematic diagram of an activation system of an adjustable annuloplasty system 100 according to one embodiment. As schematically illustrated, the system 100 includes the adjustable annuloplasty ring 111 with heating element 112, the subcutaneous activation cable 120, the subcutaneous connector 130, the transcutaneous activation cable 153 with connectors 160 and 169, and an RF generator 171. In this example, the subcutaneous port 140 is not illustrated. Persons having skill in the art will recognize, however, that subcutaneous port 140 may provide an interface between subcutaneous connector 130 and instrument connector 160. As described with respect to FIG. 17, other embodiments provide for a direct connection between subcutaneous connector 130 and instrument connector 160 without using the subcutaneous port 140.

As schematically illustrated in FIG. 12, subcutaneous activation cable 120 may include one or more thermocouple 172 for measuring the temperature of the heating element 112 and/or other portions (e.g., the shape memory portions) of the adjustable annuloplasty ring 111. In addition, or in other embodiments, one or more thermocouples may be at least partially located within the adjustable annuloplasty ring 111 itself. Subcutaneous connector 130 may include a resistive element 174 having a predetermined value used to uniquely identify the annuloplasty ring assembly 110. In other embodiments, the resistive element 174 may be located in the subcutaneous activation cable 120 or the adjustable annuloplasty ring 111.

As schematically illustrated in FIG. 12, the RF generator 171 in certain embodiments includes a power port 175 to provide electrical power to RF generator 171, a data port 176 to provide external communications for modulation and other functions of RF generator 171, a foot switch 177 or other type of controller to turn the RF energy on and off, and an instrument connector 178 to interface with transcutaneous activation cable 153 through instrument plug 169. In one embodiment, the RF generator 171 generates an RF signal at a frequency of about 460 kHz and power levels ranging between about 0.2 Watts and 25 Watts. Other combinations of frequencies and power levels may also be used.

Figure 13:
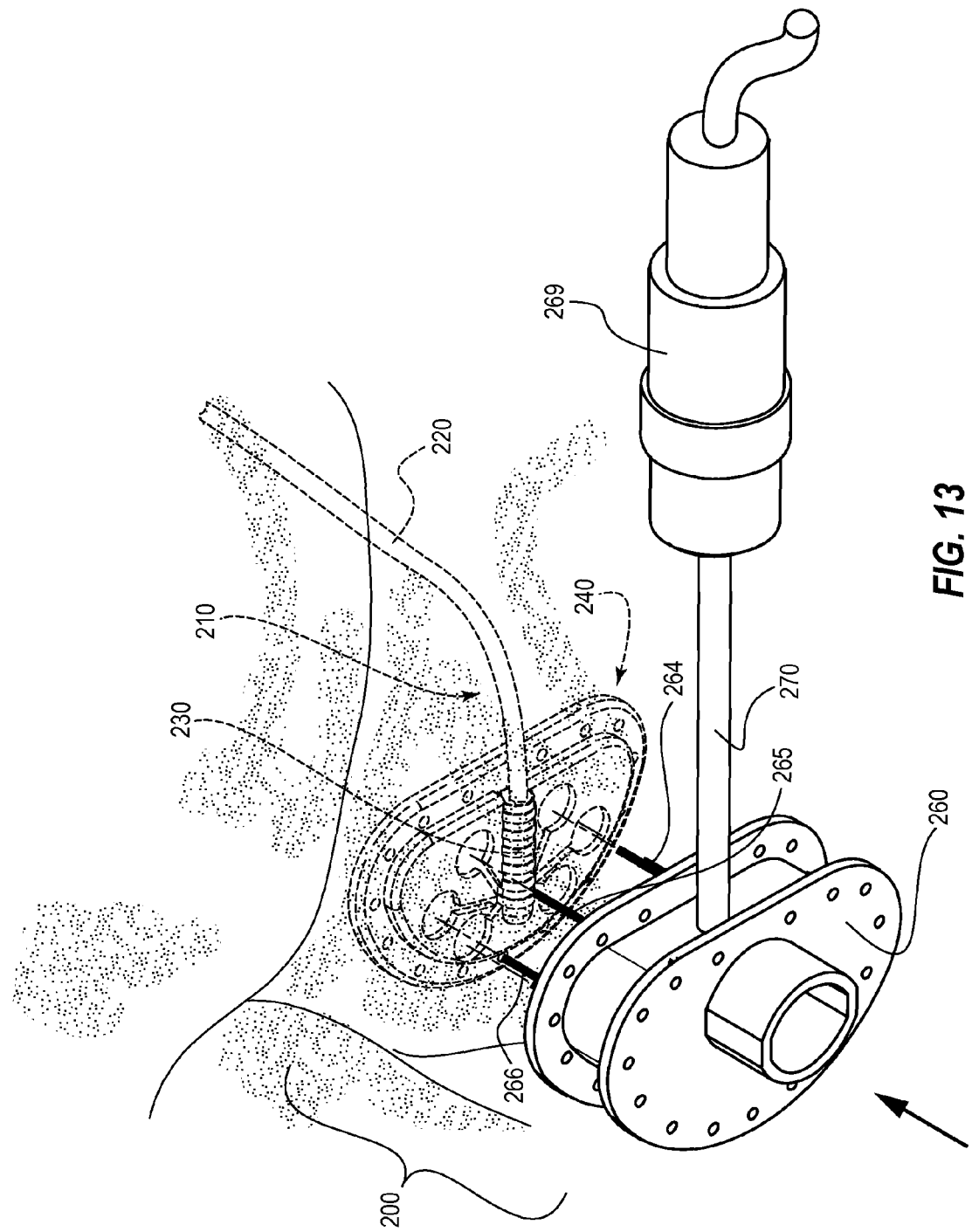
FIG. 13 is a perspective view of another embodiment of an annuloplasty ring and adjustment assembly.
Figure 14:
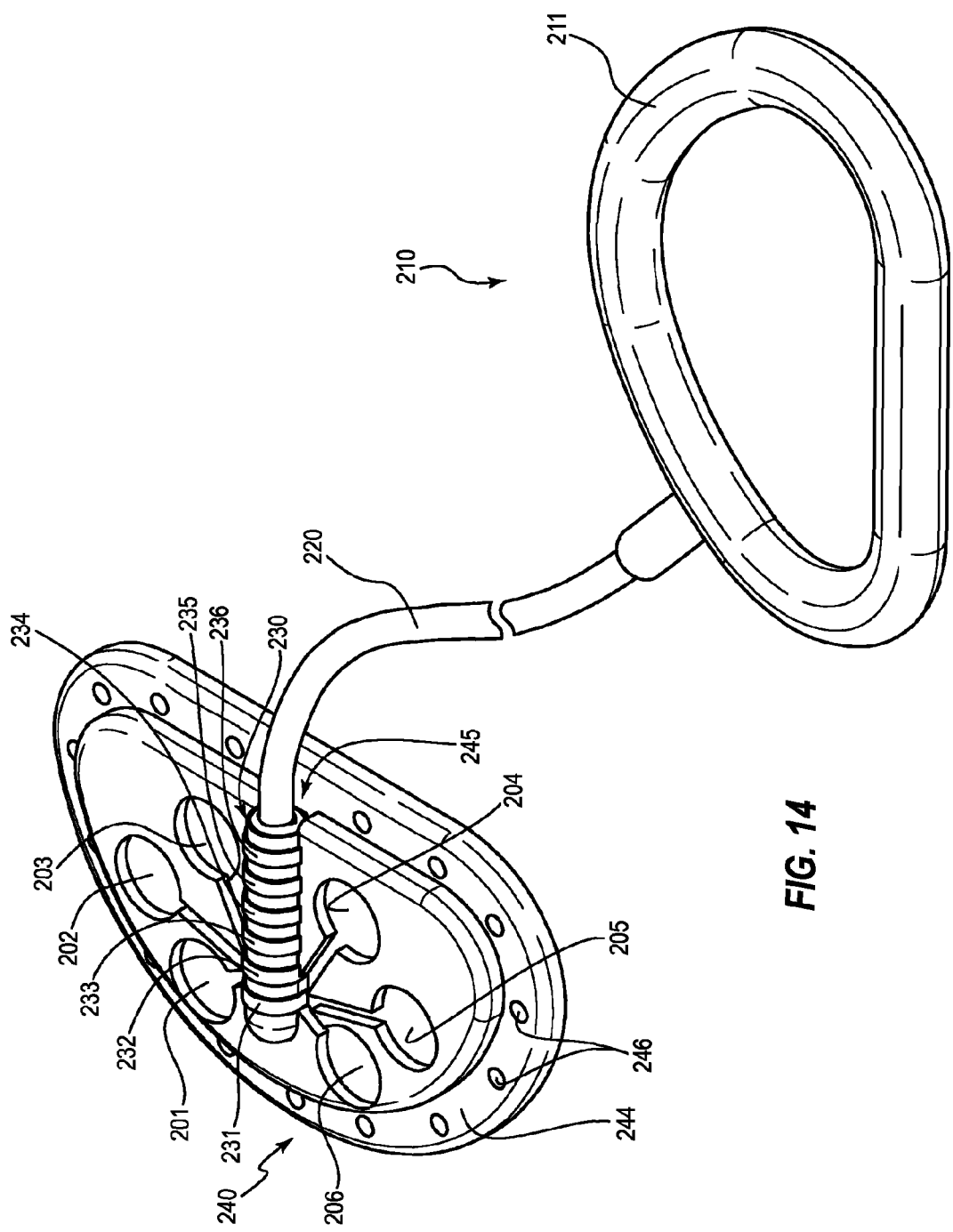
FIG. 14 is a close up perspective view of the annuloplasty ring assembly of FIG. 13.

FIGS. 13 and 14 depict another embodiment of an adjustable annuloplasty system 200, wherein system 200 resembles assembly 100, described above, in certain respects. Accordingly, like features may be designated with like reference numerals, with the leading hundreds numeral incremented from "1" to "2". Any suitable combination of the features described with respect to assembly 100 can be employed with assembly 200, and vice versa.

FIG. 13 is a perspective view of another embodiment of an adjustable annuloplasty system 200. System 200 may comprise an annuloplasty ring assembly 210 with an adjustable annuloplasty ring (not shown), and a subcutaneous activation cable 220 that ends in an in-line connector 230. A subcutaneous port 240 may be considered a portion of assembly 210, and may comprise six landing pads. The annuloplasty ring assembly 210 with subcutaneous port 240 is located subcutaneously adjacent a patient's abdomen or chest. An instrument connector 260 may comprise a plurality of protrusions 266, 265, 264 that are each configured to pierce the patient's skin and extend into the landing pads (at 201-206 in FIG. 14). Protrusions 266, 265, 264 may comprise electrodes that are configured to allow electronic communication with the annuloplasty ring via the landing pads of port 240 and cable 220. For clarity, only a subset of protrusions are visible in FIG. 13; however, one skilled in the art will recognize that the number of landing pads may typically correspond with the number of protrusions. In the depicted embodiment, there are six protrusions and six landing pads. Instrument connector 260 may be coupled to an instrument via a rigid or flexible cable 270 that can be plugged into an instrument junction 269.

Connector 260 may comprise any number of electrodes, and in the depicted embodiment, the connector comprises six electrodes, of which only three (266, 265, 264) are visible in FIG. 13. The geometry of subcutaneous port 240 and instrument connector 260 are predetermined such that the two members can be coupled together via the electrodes. The electrodes 266, 265, 264 protruding from connector 260 may be characterized as "needles" and may be insulated up to, and including a distal end of the needle. The insulation may be configured to prevent shorts when the needles are pushed into the patient's skin and tissue. The insulation may comprise a coating such as Teflon. Instrument connector 260 may comprise a rigid plastic such as polycarbonate, ABS, PolyEthereEtherKetone (PEEK), or any other suitable material.

FIG. 14 is a perspective view of annuloplasty ring assembly 210, which may comprise an adjustable annuloplasty ring 211, subcutaneous activation cable 220, subcutaneous connector 230, and subcutaneous port 240. Subcutaneous connector 230 comprises an in-line six-electrode connector. Electrodes 231-236 may be configured similarly as electrodes 131-136, described herein. Subcutaneous port 240 comprises a flange 244 and a plurality of suture apertures 246. Subcutaneous port 240 also comprises a plurality of landing pads 201-206, which are each in electronic communication with one of the electrodes 231-236 of subcutaneous connector 230. Landing pads 201-206 may be characterized as electronic connectors, and may be analogous to electronic connectors 101-106. Landing pads 201-206 may each be made watertight by employing a cap, plug, or tape to each landing pad or an entirety of subcutaneous port 240. Subcutaneous connector 230 may be inserted into port 240 via an insert aperture 245.

Figure 15:
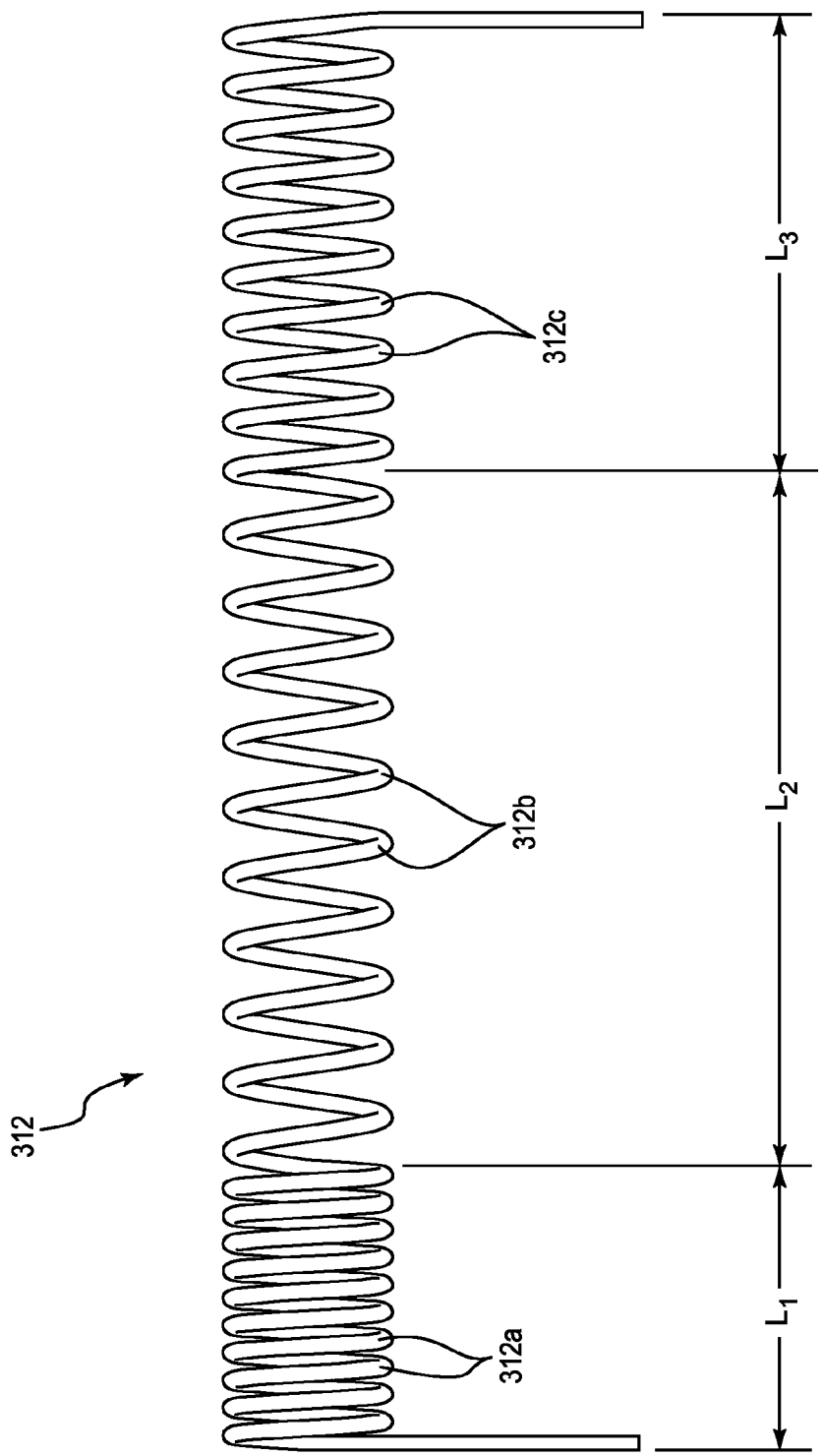
FIG. 15 is a close up perspective view of another embodiment of an arrangement of a heating element.

FIG. 15 depicts an example embodiment of a heating wire 312, wherein heating wire 312 resembles heating element 112, described above, in certain respects. Accordingly, like features may be designated with like reference numerals, with the leading hundreds numeral incremented from "1" to "3". Any suitable combination of the features described with respect to heating element 112 can be employed with heating wire 312, and vice versa.

Heating wire 312 may be configured as a plurality of coils. Heating wire 312 may be characterized as a variable pitch power heating element. As described herein, the size and shape of the adjustable annuloplasty ring may be altered by applying heat to the ring. The size and/or shape of the adjustable annuloplasty ring may be asymmetrically altered by asymmetrically applying heat. This may be achieved by varying a density of heating coils around the shape memory core of the annuloplasty ring. In FIG. 15 one embodiment of a variable density coiled heating wire 312 is depicted, wherein the heating wire comprises three different density of coils, $L_1$, $L_2$ and $L_3$, which are illustrated by coils 312a, 312b, and 312c. Impedance of each section may vary according to use on predetermined annuloplasty rings. In one embodiment, the wire is wound over a 0.057" (+/−0.001") mandrel or pin gauge.

Figure 16:
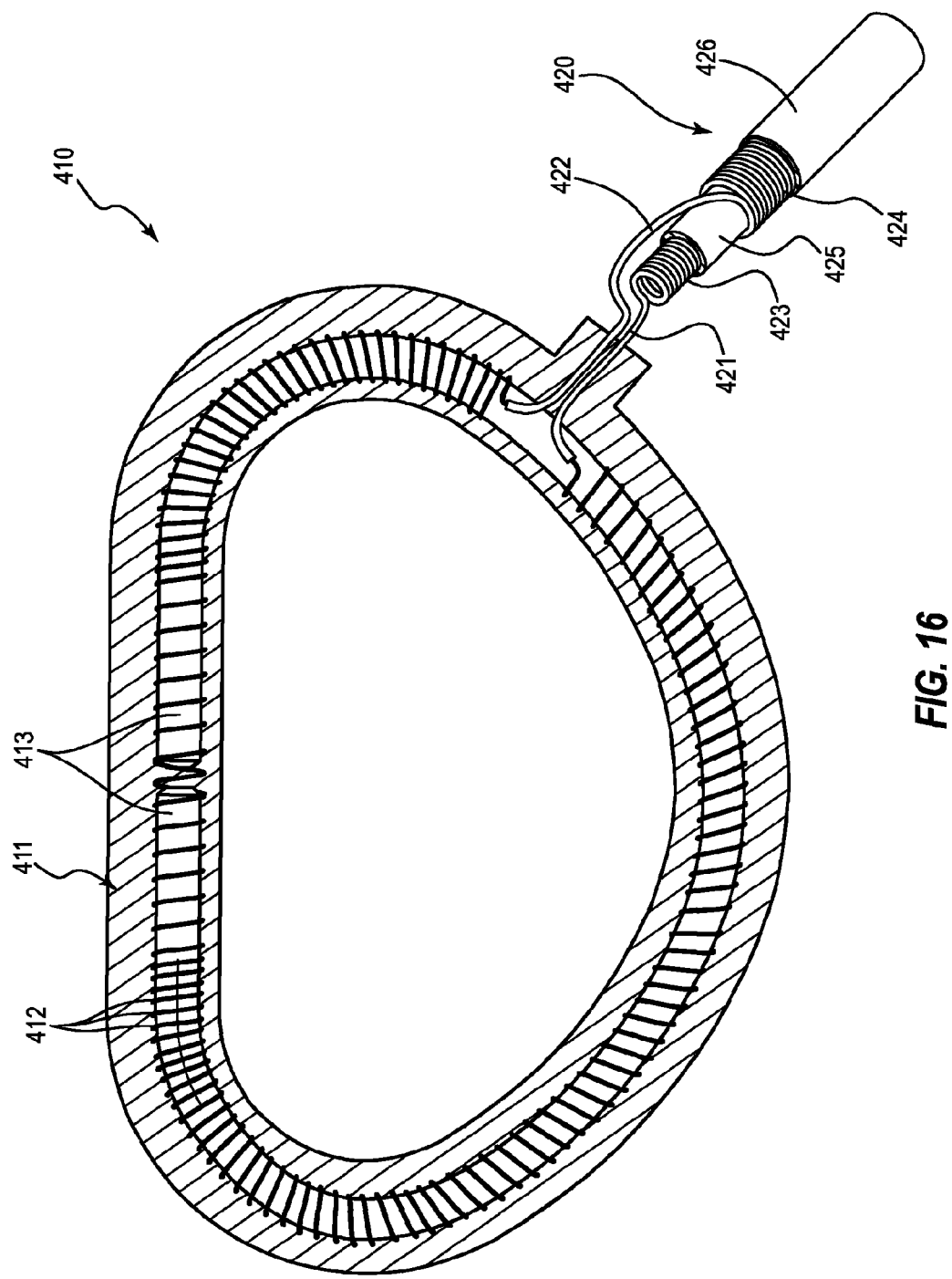
FIG. 16 is a close up cutaway view of another embodiment of an SMA annuloplasty ring assembly.

FIG. 16 depicts another embodiment of a portion of an annuloplasty ring assembly 410, wherein annuloplasty ring assembly 410 resembles annuloplasty ring assemblies 110 and 210, described above, in certain respects. Accordingly, like features may be designated with like reference numerals, with the leading hundreds numeral incremented from "1" or "2" to "4". Any suitable combination of the features described with respect to annuloplasty ring assemblies 110 and/or 210 can be employed with annuloplasty ring assembly 410, and vice versa.

FIG. 16 is a cutaway perspective view of a portion of an annuloplasty ring assembly 410. Assembly 410 may comprise a subcutaneous coaxial activation cable 420 and an adjustable annuloplasty ring 411. Adjustable annuloplasty ring 411 may comprise a shape memory core 413 and a heating wire that may be configured as coils 412 wrapped around the shape memory core 413. Coils 412 may be configured as variable density coils, wherein some portions of shape memory core 413 have a higher density of coils 412 than other portions. Thus, portions of shape memory core 413 having a higher density of coils 412 to faster or to a higher temperature than portions of the shape memory core 413 having a lower density of coils 412.

Heating coils 412 are configured as a continuous wire that is coupled to an anterior lead 421 and a posterior lead 422. Both the anterior and posterior leads 421 and 422 may be configured as protrusions of coils, wherein the anterior lead 421 extends from an inner coil 423 of coaxial cable 420, and the posterior lead 422 extends from an outer coil 424. Inner and outer coils 423 and 424 may each include multiple (e.g., four) lead wires. Inner and outer coils 423 and 424 may be separated by an inner sheath 425 and the entire cable 420 may be housed within an outer sheath 426, which may be characterized as insulation. Sheaths 425 and 426 may comprise silicone or any other suitable material. Inner coils 423 may be coiled in a round shape to form a lumen. The coiled coaxial design of subcutaneous activation cable 420 provides strength and flexibility for permanent or extended subcutaneous implantation within a patient.

FIG. 16 illustrates the leads 421, 422 exiting the adjustable annuloplasty ring 411 at a location corresponding to a P2/P3 leaflet junction of a mitral valve. This exit location facilitates routing of subcutaneous activation cable 420 through a desired location in the heart wall to avoid the coronary sinus or other structures that may be damaged by the cable 420. Persons skilled in the art will recognize, however, that the leads 421, 422 may exit the adjustable annuloplasty ring 411 from other locations. For example, in one embodiment, the leads 421, 422 exit the adjustable annuloplasty ring 411 at a location corresponding to P1/P2 leaflet junction of the mitral valve. Other locations may be selected based on patient needs and the particular heart valve being treated.

Figure 17:
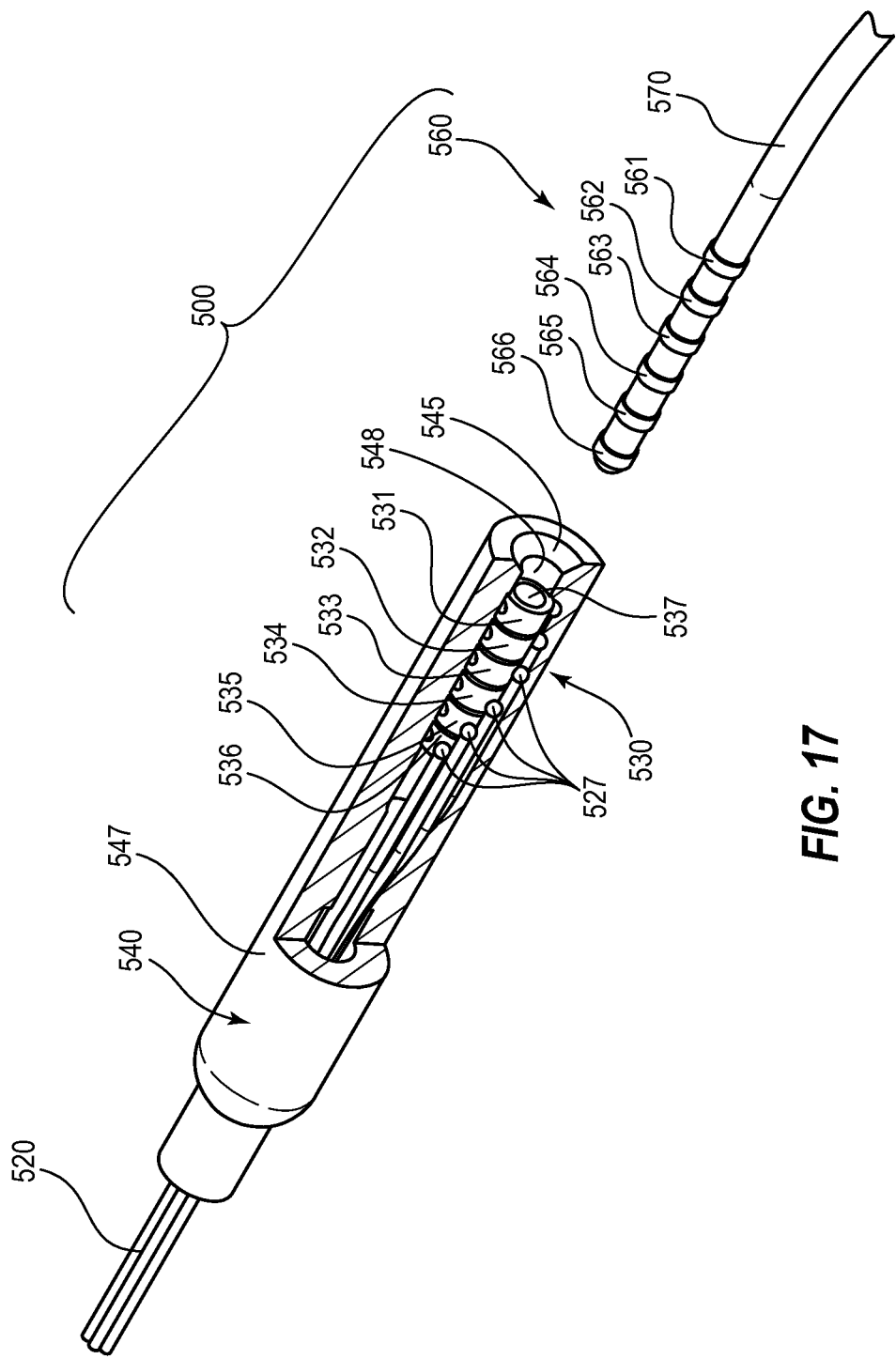
FIG. 17 is a cutaway perspective view of another embodiment of an adjustable annuloplasty ring system.

FIG. 17 depicts another embodiment of a portion of an adjustable annuloplasty system 500, wherein system 500 resembles systems 100 and/or 200, described above, in certain respects. Accordingly, like features may be designated with like reference numerals, with the leading hundreds numeral incremented from "1" or "2" to "5". Any suitable combination of the features described with respect to systems 100 and/or 200 can be employed with system 500, and vice versa.

FIG. 17 is a perspective view of a portion of another embodiment of an adjustable annuloplasty system 500. Visible in FIG. 17 are a transcutaneous activation cable 520, a transcutaneous connector 530, a port 540, an instrument connector 560, and an instrument cable 570. Although not shown, transcutaneous cable 520 couples to an adjustable annuloplasty ring. Transcutaneous cable 520 and transcutaneous connector 530 may comprise a portion of an annuloplasty ring assembly. In this embodiment, cable 520 and connector 530 are referred to as transcutaneous because during use one or both are pulled at least partially through the patient's skin. Because they are also implanted within subcutaneous tissue when not in use, they may also be referred to as subcutaneous components.

Transcutaneous cable 520 may be electronically coupled to transcutaneous connector 530 at a plurality of contact points 527, which in some embodiments may comprise solder points.

Transcutaneous cable 520 (and other cables disclosed herein, such as cables 120, 170, 220, 270, 420, and 570) may comprise the following features. The cable may comprise a combo wire that is coiled into a lead. The cable may comprise a single wire comprising stainless steel or copper. Such a single wire may be coiled into large or small coils. In one embodiment, the cable comprises stainless steel wire. In various embodiments, the wire has the following specifications: OD=0.007"; 7 wires (0.00233" OD) twisted into 1 wire (i.e.: 1×7×0.02233"; 0.007"); break load=12.55 lbs; yield load=10.34 lbs; yield strength=361 Kpsi; break strength=438 Kpsi; elongation=2.5%. The cable may comprise an insulated silicone tube over top of coil; a combined wire coil over silicone tube; and/or an insulated silicone tube over top of outer coil. Coaxial lead wire may have a low profile, is flexible (coil and 7 combo wires), is durable (coil resists the dampening bending/fatigue factor), and is safe (combo wires allow safety margin for broken strands). Other embodiments of cables disclosed herein may employ different combinations of wires including, for example: 1×3; 1×7; 1×19; 3×7; 7×3; 7×7; and 7×19.

Transcutaneous connector 530 is in electronic communication with transcutaneous cable 520 via contact points 527, and may be characterized as a "female" connector. Transcutaneous connector 530 comprises $1^{st}$-$6^{th}$ electrodes 531-536. Each electrode 531-536 is coupled to a wire of transcutaneous cable 520 at contact points 527. Transcutaneous connector 530 comprises an aperture 537 for receiving an instrument connector. An interior of female transcutaneous connector 530 may comprise interior portions of electrodes 531-536 or an electrically conductive material such that the interior of transcutaneous connector 530 is in electronic communication with electrodes 531-536.

Port 540 may comprise a plastic or silicone member, having an aperture 545 for receiving a connector, and a chamber 548. Aperture 545 is configured to receive instrument connector 560. Port 540 may comprise a removable cap (not shown) that is coupled to the port and is configured to provide a water-tight seal with aperture 545. Aperture 545 may be configured to form a water-tight seal with instrument connector 560 after the connector has been inserted into female ring connector 530. Chamber 548 is configured to enclose and house female connector 530. Transcutaneous connector 530 and port 540 may comprise a single member, wherein transcutaneous connector 530 and port 540 are manufactured together. Alternatively, port 540 may comprise a container for transcutaneous connector 530, which for instance, can be slid up cable 520 to cover connector 530. One skilled in the art will recognize that a variety of types and configurations of ports and connectors may be employed without departing from the spirit of the present disclosure. For example, the connectors may resemble the contact systems of some pace maker devices, such as the Hypertac High Performance Contact System that is manufactured by Hypertronics Corporation of Hudson, Mass.

Instrument connector 560 may comprise a six-lead in-line connector. Instrument connector 560 may comprise $1^{st}$-$6^{th}$ electrodes 561-566. Instrument connector 560 is configured as a male connector and is configured to be received by female transcutaneous connector 530 such that a friction or interference fit is achieved by the interior of the female connector and electrodes 561-566 of the male connector. Male connector 560 is in electronic communication with an instrument cable 570, which may to extend to an instrument, such as an RF generator.

Port 540 with transcutaneous connector 530 may be implanted within subcutaneous tissue when the adjustable annuloplasty ring is implanted within the patient's heart. A surgeon may postoperatively access port 540 by making an incision in the patient's skin and pulling at least a portion of the port 540, transcutaneous connector 530, and/or transcutaneous cable through the incision so as to be external to the patient's body. The surgeon may then remove the protective cap from port 540 and insert the male instrument connector 560 into the female transcutaneous connector 530. After adjusting the annuloplasty ring, the surgeon may then replace the cap, reinsert the port 540 into the subcutaneous tissue, and repair the incision.

FIG. 17 shows port 540 as including a female connector and instrument connector 560 as being a male connector. In other embodiments, however, a male connector coupled through a lead or cable to an annuloplasty ring may be implanted in subcutaneous tissue and later pulled through the skin for external coupling to a female instrument connector.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Further, many modifications may be made to the illustrated annuloplasty ring embodiments. For example, in some embodiments, the annuloplasty ring includes an energy absorbing material to increase heating efficiency and localize heating in the area of the shape memory material. Thus, damage to the surrounding tissue is reduced or minimized. Energy absorbing materials for light or laser activation energy may include nanoshells, nanospheres and the like, particularly where infrared laser energy is used to energize the material. Such nanoparticles can be made from a dielectric, such as silica, coated with an ultra thin layer of a conductor, such as gold, and be selectively tuned to absorb a particular frequency of electromagnetic radiation. In some embodiments, the nanoparticles range in size between about 5 nm and about 20 nm and can be suspended in a suitable material or solution, such as saline solution. Coatings comprising nanotubes or nanoparticles can also be used to absorb energy from, for example, HIFU, MRI, inductive heating, or the like.

In some embodiments, thin film deposition or other coating techniques such as sputtering, reactive sputtering, metal ion implantation, physical vapor deposition, and chemical deposition can be used to cover portions or all of the annuloplasty ring. Such coatings can be either solid or microporous. When HIFU energy is used, for example, a microporous structure traps and directs the HIFU energy toward the shape memory material. The coating improves thermal conduction and heat removal. In certain embodiments, the coating also enhances radio-opacity of the annuloplasty ring implant. Coating materials can be selected from various groups of biocompatible organic or non-organic, metallic or non-metallic materials such as titanium nitride (TiN), iridium oxide (Irox), carbon, platinum black, titanium carbide (TiC) and other materials used for pacemaker electrodes or implantable pacemaker leads. Other materials discussed herein or known in the art can also be used to absorb energy.

In addition, or in other embodiments, fine conductive wires such as platinum coated copper, titanium, tantalum, stainless steel, gold, or the like, are wrapped around the shape memory material to allow focused and rapid heating of the shape memory material while reducing undesired heating of surrounding tissues. As another example, the shape memory material can be coated with a photodynamic absorbing material which is activated to heat the shape memory material when illuminated by light from a laser diode or directed to the coating through fiber optic elements in a subcutaneous activation cable. In some embodiments, the photodynamic absorbing material includes one or more drugs that are released when illuminated by the laser light.

In some embodiments, activation of the shape memory material is synchronized with the heart beat during an imaging procedure. For example, the energy may be gated with a signal that represents the cardiac cycle such as an electrocardiogram signal. In some embodiments, the synchronization and gating is configured to allow delivery of energy to the shape memory materials at specific times during the cardiac cycle to avoid or reduce the likelihood of causing arrhythmia or fibrillation during vulnerable periods. For example, the energy can be gated so as to only expose the patient's heart to the energy during the T wave of the electrocardiogram signal.

As discussed above, shape memory materials include, for example, polymers, metals, and metal alloys including ferromagnetic alloys. Example shape memory polymers that are usable for certain embodiments of the present disclosure are disclosed by Langer, et al. in U.S. Pat. No. 6,720,402, issued Apr. 13, 2004, U.S. Pat. No. 6,388,043, issued May 14, 2002, and U.S. Pat. No. 6,160,084, issued Dec. 12, 2000, each of which are hereby incorporated by reference herein. Shape memory polymers respond to changes in temperature by changing to one or more permanent or memorized shapes. In some embodiments, the shape memory polymer is heated to a temperature between approximately 38° C. and approximately 60° C. In certain other embodiments, the shape memory polymer is heated to a temperature in a range between approximately 40. ° C. and approximately 55° C. In some embodiments, the shape memory polymer has a two-way shape memory effect wherein the shape memory polymer is heated to change it to a first memorized shape and cooled to change it to a second memorized shape. The shape memory polymer can be cooled, for example, by inserting or circulating a cooled fluid through a catheter or through a lumen within the subcutaneous activation cable.

Shape memory polymers implanted in a patient's body can be heated using, for example, external light energy sources such as infrared, near-infrared, ultraviolet, microwave and/or visible light sources. In some embodiments, the light energy is selected to increase absorption by the shape memory polymer and reduce absorption by the surrounding tissue. Thus, damage to the tissue surrounding the shape memory polymer is reduced when the shape memory polymer is heated to change its shape.

Certain metal alloys have shape memory qualities and respond to changes in temperature and/or exposure to magnetic fields. Exemplary shape memory alloys that respond to changes in temperature include titanium-nickel (nitinol), copper-zinc-aluminum, copper-aluminum-nickel, iron-manganese-silicon, iron-nickel-aluminum, gold-cadmium, combinations of the foregoing, and the like. In some embodiments, the shape memory alloy comprises a biocompatible material such as a titanium-nickel alloy.

Shape memory alloys exist in two distinct solid phases called martensite and austenite. The martensite phase is relatively soft and easily deformed, whereas the austenite phase is relatively stronger and less easily deformed. For example, shape memory alloys enter the austenite phase at a relatively high temperature and the martensite phase at a relatively low temperature. Shape memory alloys begin transforming to the martensite phase at a start temperature ($M_s$) and finish transforming to the martensite phase at a finish temperature ($M_f$). Similarly, such shape memory alloys begin transforming to the austenite phase at a start temperature ($A_s$) and finish transforming to the austenite phase at a finish temperature ($A_f$). Both transformations have a hysteresis. Thus, the $M_s$ temperature and the $A_f$ temperature are not coincident with each other, and the $M_f$ temperature and the $A_s$ temperature are not coincident with each other.

In some embodiments, the shape memory alloy is processed to form a memorized shape in the austenite phase in the form of a ring or partial ring. The shape memory alloy is then cooled below the $M_f$ temperature to enter the martensite phase and deformed into a larger or smaller ring. For example, in some embodiments, the shape memory alloy is formed into a ring or partial ring that is larger than the memorized shape but still small enough to improve leaflet coaptation and reduce regurgitation in a heart valve upon being attached to the heart valve annulus. In some embodiments, the shape memory alloy is sufficiently malleable in the martensite phase to allow a user such as a physician to adjust the circumference of the ring in the martensite phase by hand to achieve a desired fit for a particular heart valve annulus. After the ring is attached to the heart valve annulus, the circumference of the ring can be adjusted non-invasively by heating the shape memory alloy to an activation temperature (e.g., temperatures ranging from the $A_s$ temperature to the $A_f$ temperature).

Thereafter, when the shape memory alloy is exposed to a temperature elevation and transformed to the austenite phase, the alloy changes in shape from the deformed shape to the memorized shape. Activation temperatures at which the shape memory alloy causes the shape of the annuloplasty ring to change shape can be selected and built into the annuloplasty ring such that collateral damage is reduced or eliminated in tissue adjacent the annuloplasty ring during the activation process. Example $A_f$ temperatures for suitable shape memory alloys range between approximately 45° C. and approximately 70° C. Furthermore, example $M_s$ temperatures range between approximately 10° C. and approximately 20° C., and example $M_f$ temperatures range between approximately −1° C. and approximately 15° C. The size of the annuloplasty ring can be changed all at once or incrementally in small steps at different times in order to achieve the adjustment necessary to produce the desired clinical result.

In some embodiments, combinations of different shape memory materials are used. For example, in some embodiments, annuloplasty rings can comprise a combination of shape memory polymer and shape memory alloy (e.g., NiTi). In some embodiments, an annuloplasty ring comprises a shape memory polymer tube and a shape memory alloy (e.g., NiTi) disposed within the tube. Such embodiments are flexible and allow the size and shape of the shape memory to be further reduced without impacting fatigue properties. In some embodiments, shape memory polymers are used with shape memory alloys to create a bi-directional (e.g., capable of expanding and contracting) annuloplasty ring. Bi-directional annuloplasty rings can be created with a wide variety of shape memory material combinations having different characteristics.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the invention. Embodiments of the invention in which an exclusive property or privilege is claimed are defined as follows.

The invention claimed is:
1. An annuloplasty ring assembly, comprising:
   an adjustable annuloplasty ring including a body member comprising shape memory material to change a dimension of the adjustable annuloplasty ring in response to application of an activation energy;
   a subcutaneous activation cable to provide the activation energy to the shape memory material of the adjustable annuloplasty ring, the subcutaneous activation cable comprising:

a first end coupled to the adjustable annuloplasty ring; and
a second end comprising a subcutaneous connector including a first plurality of electrodes,
wherein the subcutaneous connector comprises an in-line connector such that the first plurality of electrodes comprise electrically conductive bands arranged along an axis of the subcutaneous activation cable to form a male connector; and
a subcutaneous port implantable in subcutaneous tissue within a patient, the subcutaneous port comprising:
a first interface to receive the subcutaneous connector of the subcutaneous activation cable;
a second interface to receive a transcutaneous connector inserted through the patient's skin, the transcutaneous connector providing the activation energy to the subcutaneous port through a second plurality of electrodes; and
a plurality of electrical interconnections to establish electrical communication between the first plurality of electrodes of the subcutaneous connector and respective ones of the second plurality of electrodes of the transcutaneous connector,
wherein the first interface of the subcutaneous port comprises a first aperture providing access to a first channel within the subcutaneous port to form a female connector that receives the male in-line connector of the subcutaneous connector and establishes an electrical connection between the first plurality of electrodes and respective ones of the plurality of electrical interconnections of the subcutaneous port,
wherein the second interface of the subcutaneous port comprises a second aperture providing access to a second channel within the subcutaneous port to form a female connector that receives a male in-line connector of the transcutaneous connector and establishes an electrical connection between the second plurality of electrodes and respective ones of the plurality of electrical interconnections of the subcutaneous port,
wherein the first aperture of the first interface and the second aperture of the second interface are located on opposing sides of the subcutaneous port, and
wherein an axis of the first channel is in a first plane, an axis of the second channel is in a second plane, and the first plane is parallel to the second plane.

2. The annuloplasty ring assembly of claim 1, wherein the subcutaneous port comprises a plurality of suture apertures that are each configured to receive a suture to attach the subcutaneous port to the subcutaneous tissue.

3. The annuloplasty ring assembly of claim 2, wherein the suture apertures are located on a flange of the port, and wherein the flange extends away from the port.

4. The annuloplasty ring assembly of claim 1, wherein the adjustable annuloplasty ring further comprises a heating element coiled around at least a portion of the body member comprising the shape memory material, wherein the activation energy comprises radio frequency (RF) energy, and wherein the heating element generates thermal energy in response to receiving the RF energy through the subcutaneous activation cable.

5. The annuloplasty ring assembly of claim 4, wherein the heating element comprises a variable density coil that transfers thermal energy to the body member at a higher rate in areas corresponding to relatively higher coil densities.

6. The annuloplasty ring assembly of claim 1, wherein the subcutaneous activation cable comprises a coaxial cable comprising an inner coil and an outer coil separated from one another by an insulator.

7. The annuloplasty ring assembly of claim 1, wherein the first end of the subcutaneous activation cable is coupled to the adjustable annuloplasty ring at a location corresponding to a P2/P3 leaflet junction of a mitral valve when the adjustable annuloplasty ring is implanted around the annulus of the mitral valve.

8. The annuloplasty ring assembly of claim 1, wherein the first end of the subcutaneous activation cable is coupled to the adjustable annuloplasty ring at a location corresponding to a P1/P2 leaflet junction of a mitral valve when the adjustable annuloplasty ring is implanted around the annulus of the mitral valve.

9. The annuloplasty ring assembly of claim 1, further comprising a thermocouple to measure a temperature within the adjustable annuloplasty ring, the subcutaneous activation cable further comprising one or more leads for communicating signals between the thermocouple and the subcutaneous port.

10. The annuloplasty ring assembly of claim 1, further comprising a resistive element with a resistive value selected to uniquely identify at least one of the adjustable annuloplasty ring and the subcutaneous activation cable.

11. An annuloplasty ring assembly, comprising:
an adjustable annuloplasty ring including a body member comprising shape memory material to change a dimension of the adjustable annuloplasty ring in response to application of an activation energy;
a subcutaneous activation cable to provide the activation energy to the shape memory material of the adjustable annuloplasty ring, the subcutaneous activation cable comprising:
a first end coupled to the adjustable annuloplasty ring; and
a second end comprising a subcutaneous connector including a first plurality of electrodes,
wherein the subcutaneous connector comprises an in-line connector such that the first plurality of electrodes comprise electrically conductive bands arranged along an axis of the subcutaneous activation cable to form a male connector; and
a subcutaneous port implantable in subcutaneous tissue within a patient, the subcutaneous port comprising:
a first interface to receive the subcutaneous connector of the subcutaneous activation cable;
a second interface to receive a transcutaneous connector inserted through the patient's skin, the transcutaneous connector providing the activation energy to the subcutaneous port through a second plurality of electrodes; and
a plurality of electrical interconnections to establish electrical communication between the first plurality of electrodes of the subcutaneous connector and respective ones of the second plurality of electrodes of the transcutaneous connector,
wherein the first interface of the subcutaneous port comprises a first aperture providing access to a first channel within the subcutaneous port to form a female connector that receives the male in-line connector of the subcutaneous connector and establishes an electrical connection between the first plurality of electrodes and respective ones of the plurality of electrical interconnections of the subcutaneous port,
wherein the second interface of the subcutaneous port comprises a second aperture providing access to a second channel within the subcutaneous port to form a female connector that receives a male in-line connector of the transcutaneous connector and establishes an electrical connection between the second plurality of electrodes and respective ones of the plurality of electrical interconnections of the subcutaneous port, wherein an axis of the first channel is at an angle with respect to an axis of the second channel such that implanting the subcutaneous port within the subcutaneous tissue of the patient with the axis of the first channel pointing substantially parallel to a surface of the patient's skin results in the axis of the second channel pointing, at an angle with respect to the surface of the patient's skin, toward the surface of the patient's skin to thereby provide access to the second aperture through a trocar or needle from the surface of the patient's skin.

12. The annuloplasty ring assembly of claim 11, wherein the subcutaneous port further comprises a slanted target area that funnels the trocar or needle into the second aperture.

13. The annuloplasty ring assembly of claim 11, wherein the first end of the subcutaneous activation cable is coupled to the adjustable annuloplasty ring at a location corresponding to a P2/P3 leaflet junction of a mitral valve when the adjustable annuloplasty ring is implanted around the annulus of the mitral valve.

14. The annuloplasty ring assembly of claim 11, wherein the first end of the subcutaneous activation cable is coupled to the adjustable annuloplasty ring at a location corresponding to a P1/P2 leaflet junction of a mitral valve when the adjustable annuloplasty ring is implanted around the annulus of the mitral valve.

15. The annuloplasty ring assembly of claim 11, further comprising a thermocouple to measure a temperature within the adjustable annuloplasty ring, the subcutaneous activation cable further comprising one or more leads for communicating signals between the thermocouple and the subcutaneous port.

16. An annuloplasty ring assembly, comprising:
an adjustable annuloplasty ring including a body member comprising shape memory material to change a dimension of the adjustable annuloplasty ring in response to application of an activation energy;
a subcutaneous activation cable to provide the activation energy to the shape memory material of the adjustable annuloplasty ring, the subcutaneous activation cable comprising:
a first end coupled to the adjustable annuloplasty ring; and
a second end comprising a subcutaneous connector including a first plurality of electrodes; and
a subcutaneous port implantable in subcutaneous tissue within a patient, the subcutaneous port comprising:
a first interface to receive the subcutaneous connector of the subcutaneous activation cable;
a second interface to receive a transcutaneous connector inserted through the patient's skin, the transcutaneous connector providing the activation energy to the subcutaneous port through a second plurality of electrodes;
a plurality of electrical interconnections to establish electrical communication between the first plurality of electrodes of the subcutaneous connector and respective ones of the second plurality of electrodes of the transcutaneous connector; and
a heating element coiled around at least a portion of the body member comprising the shape memory material, wherein the activation energy comprises radio frequency (RF) energy, and wherein the heating element generates thermal energy in response to receiving the RF energy through the subcutaneous activation cable, wherein the heating element comprises a variable density coil that transfers thermal energy to the body member at a higher rate in areas corresponding to relatively higher coil densities.

17. The annuloplasty ring assembly of claim 16, wherein the subcutaneous connector comprises an in-line connector such that the first plurality of electrodes comprise electrically conductive bands arranged along an axis of the subcutaneous activation cable to form a male connector.

18. The annuloplasty ring assembly of claim 17, wherein the first interface of the subcutaneous port comprises a first aperture providing access to a first channel within the subcutaneous port to form a female connector that receives the male in-line connector of the subcutaneous connector and establishes an electrical connection between the first plurality of electrodes and respective ones of the plurality of electrical interconnections of the subcutaneous port.

19. The annuloplasty ring assembly of claim 18, wherein the second interface of the subcutaneous port comprises a second aperture providing access to a second channel within the subcutaneous port to form a female connector that receives a male in-line connector of the transcutaneous connector and establishes an electrical connection between the second plurality of electrodes and respective ones of the plurality of electrical interconnections of the subcutaneous port.

20. The annuloplasty ring assembly of claim 16, wherein the subcutaneous port comprises a plurality of suture apertures that are each configured to receive a suture to attach the subcutaneous port to the subcutaneous tissue.

21. The annuloplasty ring assembly of claim 20, wherein the suture apertures are located on a flange of the port, and wherein the flange extends away from the port.

22. The annuloplasty ring assembly of claim 16, wherein the first end of the subcutaneous activation cable is coupled to the adjustable annuloplasty ring at a location corresponding to a P2/P3 leaflet junction of a mitral valve when the adjustable annuloplasty ring is implanted around the annulus of the mitral valve.

23. The annuloplasty ring assembly of claim 16, wherein the first end of the subcutaneous activation cable is coupled to the adjustable annuloplasty ring at a location corresponding to a P1/P2 leaflet junction of a mitral valve when the adjustable annuloplasty ring is implanted around the annulus of the mitral valve.

24. The annuloplasty ring assembly of claim 16, further comprising a thermocouple to measure a temperature within the adjustable annuloplasty ring, the subcutaneous activation cable further comprising one or more leads for communicating signals between the thermocouple and the subcutaneous port.

25. An annuloplasty ring assembly, comprising:
an adjustable annuloplasty ring including a body member comprising shape memory material to change a dimension of the adjustable annuloplasty ring in response to application of an activation energy;
a subcutaneous activation cable to provide the activation energy to the shape memory material of the adjustable annuloplasty ring, the subcutaneous activation cable comprising:
a coaxial cable comprising an inner coil and an outer coil separated from one another by an insulator;
a first end coupled to the adjustable annuloplasty ring; and
a second end comprising a subcutaneous connector including a first plurality of electrodes; and
a subcutaneous port implantable in subcutaneous tissue within a patient, the subcutaneous port comprising:

a first interface to receive the subcutaneous connector of the subcutaneous activation cable;

a second interface to receive a transcutaneous connector inserted through the patient's skin, the transcutaneous connector providing the activation energy to the subcutaneous port through a second plurality of electrodes; and a plurality of electrical interconnections to establish electrical communication between the first plurality of electrodes of the subcutaneous connector and respective ones of the second plurality of electrodes of the transcutaneous connector.

26. The annuloplasty ring assembly of claim 25, wherein the subcutaneous connector comprises an in-line connector such that the first plurality of electrodes comprise electrically conductive bands arranged along an axis of the subcutaneous activation cable to form a male connector.

27. The annuloplasty ring assembly of claim 26, wherein the first interface of the subcutaneous port comprises a first aperture providing access to a first channel within the subcutaneous port to form a female connector that receives the male in-line connector of the subcutaneous connector and establishes an electrical connection between the first plurality of electrodes and respective ones of the plurality of electrical interconnections of the subcutaneous port.

28. The annuloplasty ring assembly of claim 27, wherein the second interface of the subcutaneous port comprises a second aperture providing access to a second channel within the subcutaneous port to form a female connector that receives a male in-line connector of the transcutaneous connector and establishes an electrical connection between the second plurality of electrodes and respective ones of the plurality of electrical interconnections of the subcutaneous port.

29. The annuloplasty ring assembly of claim 25, wherein the subcutaneous port comprises a plurality of suture apertures that are each configured to receive a suture to attach the subcutaneous port to the subcutaneous tissue.

30. The annuloplasty ring assembly of claim 29, wherein the suture apertures are located on a flange of the port, and wherein the flange extends away from the port.

31. The annuloplasty ring assembly of claim 25, wherein the first end of the subcutaneous activation cable is coupled to the adjustable annuloplasty ring at a location corresponding to a P2/P3 leaflet junction of a mitral valve when the adjustable annuloplasty ring is implanted around the annulus of the mitral valve.

32. The annuloplasty ring assembly of claim 25, wherein the first end of the subcutaneous activation cable is coupled to the adjustable annuloplasty ring at a location corresponding to a P1/P2 leaflet junction of a mitral valve when the adjustable annuloplasty ring is implanted around the annulus of the mitral valve.

33. The annuloplasty ring assembly of claim 25, further comprising a thermocouple to measure a temperature within the adjustable annuloplasty ring, the subcutaneous activation cable further comprising one or more leads for communicating signals between the thermocouple and the subcutaneous port.

34. An annuloplasty ring assembly, comprising:

an adjustable annuloplasty ring including a body member comprising shape memory material to change a dimension of the adjustable annuloplasty ring in response to application of an activation energy;

a subcutaneous activation cable to provide the activation energy to the shape memory material of the adjustable annuloplasty ring, the subcutaneous activation cable comprising:

a first end coupled to the adjustable annuloplasty ring; and a second end comprising a subcutaneous connector including a first plurality of electrodes;

a resistive element with a resistive value selected to uniquely identify at least one of the adjustable annuloplasty ring and the subcutaneous activation cable; and a subcutaneous port implantable in subcutaneous tissue within a patient, the subcutaneous port comprising:

a first interface to receive the subcutaneous connector of the subcutaneous activation cable;

a second interface to receive a transcutaneous connector inserted through the patient's skin, the transcutaneous connector providing the activation energy to the subcutaneous port through a second plurality of electrodes; and a plurality of electrical interconnections to establish electrical communication between the first plurality of electrodes of the subcutaneous connector and respective ones of the second plurality of electrodes of the transcutaneous connector.

35. The annuloplasty ring assembly of claim 34, wherein the subcutaneous connector comprises an in-line connector such that the first plurality of electrodes comprise electrically conductive bands arranged along an axis of the subcutaneous activation cable to form a male connector.

36. The annuloplasty ring assembly of claim 35, wherein the first interface of the subcutaneous port comprises a first aperture providing access to a first channel within the subcutaneous port to form a female connector that receives the male in-line connector of the subcutaneous connector and establishes an electrical connection between the first plurality of electrodes and respective ones of the plurality of electrical interconnections of the subcutaneous port.

37. The annuloplasty ring assembly of claim 36, wherein the second interface of the subcutaneous port comprises a second aperture providing access to a second channel within the subcutaneous port to form a female connector that receives a male in-line connector of the transcutaneous connector and establishes an electrical connection between the second plurality of electrodes and respective ones of the plurality of electrical interconnections of the subcutaneous port.

38. The annuloplasty ring assembly of claim 34, wherein the subcutaneous port comprises a plurality of suture apertures that are each configured to receive a suture to attach the subcutaneous port to the subcutaneous tissue.

39. The annuloplasty ring assembly of claim 38, wherein the suture apertures are located on a flange of the port, and wherein the flange extends away from the port.

40. The annuloplasty ring assembly of claim 34, wherein the first end of the subcutaneous activation cable is coupled to the adjustable annuloplasty ring at a location corresponding to a P2/P3 leaflet junction of a mitral valve when the adjustable annuloplasty ring is implanted around the annulus of the mitral valve.

41. The annuloplasty ring assembly of claim 34, wherein the first end of the subcutaneous activation cable is coupled to the adjustable annuloplasty ring at a location corresponding to a P1/P2 leaflet junction of a mitral valve when the adjustable annuloplasty ring is implanted around the annulus of the mitral valve.

42. The annuloplasty ring assembly of claim 34, further comprising a thermocouple to measure a temperature within the adjustable annuloplasty ring, the subcutaneous activation cable further comprising one or more leads for communicating signals between the thermocouple and the subcutaneous port.

* * * * *